(12) United States Patent
Kaddurah-Daouk et al.

(10) Patent No.: US 8,637,321 B2
(45) Date of Patent: Jan. 28, 2014

(54) LIPIDOMICS APPROACHES FOR CENTRAL NERVOUS SYSTEM DISORDERS

(75) Inventors: Rima F. Kaddurah-Daouk, Belmont, MA (US); K. Ranga Rama Krishnan, Chapel Hill, NC (US); Joseph P. McEvoy, Durham, NC (US); Rebecca Ann Baillie, Woodland, CA (US)

(73) Assignees: Duke University, Durham, NC (US); Lipomics Technologies, Inc., Sacramento, CA (US)

( * ) Notice: Subject to any disclaimer, the term of this patent is extended or adjusted under 35 U.S.C. 154(b) by 892 days.

(21) Appl. No.: 12/091,213

(22) PCT Filed: Oct. 12, 2006

(86) PCT No.: PCT/US2006/040026
§ 371 (c)(1),
(2), (4) Date: Dec. 10, 2008

(87) PCT Pub. No.: WO2007/050318
PCT Pub. Date: May 3, 2007

(65) Prior Publication Data
US 2009/0305323 A1    Dec. 10, 2009

Related U.S. Application Data

(60) Provisional application No. 60/729,664, filed on Oct. 24, 2005, provisional application No. 60/749,691, filed on Apr. 24, 2006.

(51) Int. Cl.
*G01N 33/92*    (2006.01)

(52) U.S. Cl.
USPC ............................................. 436/71; 436/63

(58) Field of Classification Search
USPC .................................................... 436/71, 63
See application file for complete search history.

(56) References Cited

U.S. PATENT DOCUMENTS

| | | |
|---|---|---|
| 5,198,468 A | 3/1993 | Horrobin |
| 5,516,800 A | 5/1996 | Horrobin |
| 6,596,701 B1 | 7/2003 | Schwartz et al. |
| 7,005,255 B2 | 2/2006 | Kaddurah-Daouk et al. |
| 7,015,006 B1 | 3/2006 | Glen et al. |
| 7,329,489 B2 | 2/2008 | Kaddurah-Daouk et al. |
| 7,550,258 B2 | 6/2009 | Kaddurah-Daouk et al. |
| 7,550,260 B2 | 6/2009 | Kaddurah-Daouk et al. |
| 7,553,616 B2 | 6/2009 | Kaddurah-Daouk et al. |
| 7,635,556 B2 | 12/2009 | Kaddurah-Daouk et al. |
| 7,682,783 B2 | 3/2010 | Kaddurah-Daouk et al. |
| 7,682,784 B2 | 3/2010 | Kaddurah-Daouk et al. |
| 2002/0009740 A1 | 1/2002 | Kaddurah-Daouk et al. |
| 2004/0024065 A1 | 2/2004 | Watkins et al. |
| 2004/0126366 A1 | 7/2004 | Kaddurah-Daouk et al. |
| 2004/0143461 A1 | 7/2004 | Watkins |
| 2004/0146853 A1 | 7/2004 | Kaddurah-Daouk et al. |
| 2005/0009005 A1 | 1/2005 | Watkins |
| 2005/0014132 A1 | 1/2005 | Kaddurah-Daouk et al. |
| 2006/0084129 A1 | 4/2006 | Watkins |
| 2006/0088860 A1 | 4/2006 | Watkins et al. |
| 2006/0134676 A1 | 6/2006 | Kaddurah-Daouk et al. |
| 2006/0134677 A1 | 6/2006 | Kaddurah-Daouk et al. |
| 2006/0134678 A1 | 6/2006 | Kaddurah-Daouk et al. |
| 2006/0141550 A1 | 6/2006 | Watkins et al. |
| 2006/0241021 A1 | 10/2006 | Kaddurah-Daouk et al. |
| 2007/0026389 A1 | 2/2007 | Kaddurah-Daouk et al. |
| 2007/0027090 A1 | 2/2007 | Kaddurah-Daouk et al. |
| 2007/0072203 A1 | 3/2007 | Kaddurah-Daouk et al. |
| 2007/0172820 A1 | 7/2007 | Kaddurah-Daouk et al. |
| 2007/0172885 A1 | 7/2007 | Kaddurah-Daouk et al. |
| 2007/0178599 A1 | 8/2007 | Kaddurah-Daouk et al. |
| 2009/0017464 A1 | 1/2009 | Kaddurah-Daouk et al. |
| 2009/0221706 A1 | 9/2009 | Kaddurah-Daouk et al. |
| 2009/0280521 A1 | 11/2009 | Kaddurah-Daouk et al. |

FOREIGN PATENT DOCUMENTS

| | | |
|---|---|---|
| WO | WO 01/78652 A2 | 10/2001 |
| WO | WO 2004/038381 A2 | 5/2004 |

OTHER PUBLICATIONS

Vlachoyiannopoulos et al. "Atherosclerosis in premenopausal women with antiphospholipid syndrome and systemic lupus erythematosus: a controlled study", Rheumatology, 2003, 42:645-651.*

Horrobin et al. "Clozapine: elevation of membrane unsaturated lipid levels as a new mechanism of action", Schizophrenia Research, 1997, 24(1-2):214.*

Dursun et al. "The effects of clozapine on levels of total cholesterol and related lipids in serum of patients with schizophrenia: a prospective study", J of Psychiatry & Neuroscience, 1999, 24(5):453-455.*

(Continued)

*Primary Examiner* — Bin Shen
(74) *Attorney, Agent, or Firm* — Myers Bigel Sibley & Sajovec, PA

(57) ABSTRACT

The present invention has utilized the power of lipidomics to profile lipid metabolites and to characterize changes in lipid metabolism as they relate to CNS disorders. Lipidomic signatures can guide the development of diagnostic, prognostic and surrogate markers for CNS disorders; identification of new targets for drug design based on highlighted perturbed pathways; stratify patients with CNS disorders as to which pathways are impaired, and facilitate the determination of which patients with CNS disorders are candidates for a particular therapy, i.e. provide the tools for a personalized approach to therapy; identify which patients are responding or are developing side effects to a treatment; design of modified antipsychotics that have less metabolic side effects and enhanced activity; overcome the lag phase in response to some treatments; and find better combination therapies for CNS disorders that target the pathways that are impaired (e.g., impairments in lipid and/or carbohydrate metabolism).

40 Claims, 8 Drawing Sheets

(56) References Cited

OTHER PUBLICATIONS

Cuesta-Munoz et al. "Severe persistent hyperinsulinemic hypoglycemia due to a De Novo glucokinase mutation", Diabetes,2004, 53:2164-2168.*
Fenton et al. "Essential fatty acids, lipid membrane abnormalities, and the diagnosis and treatment of Schizophrenia", Biol Psychiatry, 2000:47:8-21.*
Clark "Consensus development conference on antipsychotic drugs and obesity and diabetes", Diabetes Care, 2004, 27(2):596-601.*
Atmaca M., "Serum Leptin and Triglyceride Levels in Patients on Treatment With Atypical Antipsychotics", *J Clin Psychiatry* 64:5, May 2003, pp. 598-604.
Atmaca M., et al. "Serum leptin and cholesterol levels in schizophrenic patients with and without suicide attempts", Acta Psychiar Scand 2003: 108 208-214, ISSN 0001-690X, pp. 208-214, Blackwell Munksgaard 2003.
Atmaca, M. Letter to the Editors—Weight gain, serum leptin and triglyceride levels in patients with schizophrenia on antipsychotic treatment with quetiapine, olanzapine and haloperidol, *Schizophrenia Research* 60 (2003) 99-100, Elsevier Science B.V.
Barak et al., "Effects of Olanzapine on Lipid Abnormalities in Elderly Psychotic Patients", *Drugs Aging* 2003: 20 (12) Adis Data Information BV 2003, pp. 893-896.
Baymiller et al., "Serum glucose and lipid changes during the course of clozapine treatment: the effect of concurrent β-adrenergic antagonist treatment", *Schizophrenia Research* 59 (2002) 49-57, Elsevier Science B.V.
Beasley et al., "Reductions in cholesterol and synaptic markers in association cortex in mood disorders", *Bipolar Disorders* 2005: 7: 449-455, Blackwell Munksgaard, 2005.
Brindle et al., "Application of chemometrics to H NMR spectroscopic data to investigate a relationship between human serum metabolic profiles and hypertension", *Analyst*, 2003, 128, 32-36.
Brindle et al., "Rapid and noninvasive diagnosis of the presence and severity of coronary heart disease using H-NMR-based metabonomics", *Nature Medicine*, vol. 8, No. 12, Dec. 2002, pp. 1439-1444.
Caniato et al., "Effect of omega-3 fatty acids on the lipid profile of patients taking clozapine" *Australian and New Zealand Journal of Psychiatry* 2006; 40:691-697.
Casey, "Dyslipidemia and Atypical Antipsychotic Drugs", *J Clin Psychiatry* 2004; 65 (suppl 18) pp. 27-35.
De Hert et al., "A Case Series: Evaluation of the Metabolic Safety of Aripiprazole" *Schizophrenia Bulletin* doi:10.1093/schbul/sbl037, Published by Oxford University Press on behalf of the Maryland Psychiatric Research Center, pp. 1-8, 2007.
Dunne, "Metabolites from cerebrospinal fluid in aneurismal subarachnoid haemorrage correlate with vasospasm and clinical outcome: a pattern-recognition $^1$H NMR study", *NMR in Biomedicine, NMR Biomed.* 2005; 18:24-33, Published online Sep. 29, 2004 in Wiley InterScience (www.interscience.wiley.com) DOI:10.1002/nbm.918.
Dursun et al. "The effects of clozapine on levels of total cholesterol and related lipids in serum of patients with schizophrenia: a prospective study", *Journal of Psychiatry & Neuroscience*; Nov. 1999, vol. 24, Issue 5, p. 453, 3p, 1 graph; CMA Media Inc.
Fan, "Higher fasting serum insulin levels are associated with a better psychopathology profile in acutely ill non-diabetic inpatients with schizophrenia", *Schizophrenia Research* 86 (2006) 30-35; doi: 10.1016/j.schres.2006.04.010.
Ferno et al., "Antipsychotic drugs activate SREBP-regulated expression of lipid biosynthetic genes in cultured human glioma cells: a novel mechanism of action?", *The Pharmacogenomics Journal*, (2005) 5, 298-304.
Garyfallos, Case Report—"Olanzapine versus resperidone: weight gain and elevation of serum triglyceride levels", *European Psychiatry 18* (2003) 320-321; 2003 Editions scientifiques et medicales Elsevier SAS.

German et al.,"Metabolomics: building on a century of biochemistry to guide human health", *Metobolomics*, vol. 1. No. 1, Jan. 2005, pp. 3-9. DOI 10.1007/s11306-005-1102-8, Springer Science + Business Media, Inc.
German et al., *Symposium: Improving Human Nutrition through Genomics, Proteomics and Biotechnologies*, "Personal Metabolomics as a Next Generation Nutritional Assessment [1, 2]", *JN the Journal of Nutrition*, pp. 4260-4266. 2003 American Society for Nutritional Sciences.
Henderson, "Clozapine: Diabetes Mellitus, Weight Gain, and Lipid Abnormalities", *J Clin Psychiatry* 2001; 62 (suppl 23); From the Department of Psychiatry and the Schizophrenia Program, Massachusetts General Hospital and Harvard Medical School, Boston; Presented at the symposium "Effects of Drugs on Body Weight and Glucose Regulation", Dec. 16, 2000; New York University School of Medicine, New York; pp. 39-44.
Hennen et al., "Weight Gain During Treatment of Bipolar I Patients With Olanzapine", *J Clin Psychiatry* 2004; 65: 1679-1687; pp. 1679-1687.
Holmes et al., "Metabolic Profiling of CSF: Evidence That Early Intervention May Impact on Disease Progression and Outcome in Schizophrenia" *PLoS Medicine*, Aug. 2006, vol. 3, Issue 8, pp. 1420-1428.
Horrobin et al., "Essential Fatty Acids in Plasma Phospholipids in Schizophrenics" *Biol Psychiatry*, 1989;25:562-568.
Horrobin et al., "Fatty Acid Levels in the Brains of Schizophrenics and Normal Controls" *Biol Psychiatry* 1991:30:795-805.
Horrobin, "Schizophrenia as a membrane lipid disorder which is expressed throughout the body" *Prostaglandins, Leukotrienes and Essential Fatty Acids* (1996) 55(1&2), 3-7.
Horrobin, "The membrane phospholipid hypothesis as a biochemical basis for the neurodevelopmental concept of schizophrenia", *Schizophrenia Research* 30 (1998) 193-208.
Huang et al., "Serum lipid profiles and schizophrenia: Effects of conventional or atypical antipsychotic drugs in Taiwan", *Schizophrenia Research* 80 (2005) 55-59; doi: 10.1016/j.schres.2005.05001.
Jow et al., "Leptin and cholesterol levels are low in major depressive disorder, but high in Schizophrenia", *Journal of Affective Disorders* 90 (2006) 21-27; doi: 10.1016/j.jad.2005.09.015.
Kaddurah-Daouk et al., "Metabolomics: A New Approach Towards Identifying Biomarkers and Therapeutic Targets in CNS Disorders", *Metabolic Profiling*, 2004,Chapter 4, pp. 45-63, G. Harrigan et al. (eds), Klower Academic Publishers.
Kaddurah-Daouk, "Metabolic Profiling of Patients with Schizophrenia", *PLoS Medicine*, Aug. 2006, vol. 3, Issue 8, e363, pp. 1222-1223, DOI: 10.1371/journal.pmed.0030363.
Kaiya et al., "Essential and Other Fatty Acids in Plasma in Schizophrenics and Normal Individuals from Japan" *Biol Psychiatry*, 1991;30:357-362.
Kenny et al., "Novel biomarkers for pre-eclampsia detected using metabolomics and machine learning" Metabolomics Vo. 1, No. 3, Jul. 2005, DOI: 10.1007/s11306-005-0003-1, pp. 227-234.
Keshavan et al., "Erythrocyte Membrane Phospholipids in Psychotic Patients" *Psychiatry Research*, 49:89-95, 1993.
Kingsbury et al., "The Apparent Effects of Ziprasidone on Plasma Lipids and Glucose", *J Clin Psychiatry* 62:5, May 2001; pp. 347-349.
Kinon, et al., "Longitudinal Effect of Olanzapine on Fasting Serum Lipids", *Ann. N.Y. Acad. Sci.* 1032: 295-296 (2004); doi: 10.1196/annals.1314.043.
Kinon, et al., "Long-Term Olanzapine Treatment: Weight Change and Weight-Related Health Factors in Schizophrenia", *J Clin Psychiatry* 62:2, Feb. 2001; pp. 92-100.
Lindon et al., Review: "Metabonomics technologies and their applications in physiological monitoring, drug safety assessment and disease diagnosis", *Biomarkers*, vol. 9, No. 1 (Jan.-Feb. 2004) pp. 1-31, Taylor & Francis Ltd.
Mahadik et al., "Plasma membrane phospholipid and cholesterol distribution of skin fibroblasts from drug-naïve patients at the onset of psychosis", *Schizophrenia Research* 13 (1994) 239-247.
Mahakik et al., "Phospholipids in Schizophrenia", *Textbook of Schizophrenia*, 2006, Chapter 7, pp. 117-135, Lieberman JA et al. (eds), American Psychiatric Publishing, Washington, D.C.

(56) References Cited

OTHER PUBLICATIONS

McQuade et al., A Comparison of Weight Change During Treatment With Olanzapine or Aripiprazole: Results From a Randomized, Double-Blind Study, *J Clin Psychiatry* 2004; 65 (suppl 18) pp. 47-56, Physicians Postgraduate Press, Inc.

Melkersson et al., "Relationship between levels of insulin or triglycerides and serum concentrations of the atypical antipsychotics clozapine and olanzapine in patients on treatment with therapeutic doses", *Psychopharmacology* (2003) 170:157-166; DOI 10.1007/s00213-003-1529-4.

Odunsi et al., "Detection of epithelial ovarian cancer using H-NMR-based metabonomics", *International Journal of Cancer*, vol. 113, Issue 5, pp. 782-788, Feb. 20, 2006.

Pettegrew et al., "Alterations in Brain High-Energy Phosphate and Membrane Phospholipid Metabolism in First-Episode, Drug-Naïve Schizophrenics" *Arch Gen Psychiatry*—vol. 48, Jun. 1991, pp. 563-568.

Prabakaran et al., "Mitochondrial dysfunction in schizophrenia: evidence for compromised brain metabolism and oxidative stress", *Molecular Psychiatry* (2004) 9, 684-697, Nature Publishing Group.

Raeder et al., "Antidepressant drugs activate SREBP and up-regulate cholesterol and fatty acid biosynthesis in human glial cells", *Neuroscience Letters* 395 (2006) 185-190.

Risérus, "Rosiglitazone Increases Indexes of Stearoyl-CoA Desaturase Activity in Humans", *Diabetes*, vol. 54, May 2005, pp. 1379-1384, The American Diabetes Association.

Rotrosen et al., "Phospholipid and Prostaglandin Hypotheses of Schizophrenia", 1987, Chapter 74, pp. 759-764, edited by Herbert Y. Meltzer, Raven Press New York.

Rozen et al., "Metabolomic analysis and signatures in motor neuron disease", *Metabolomics* vol. 1, No. 2, Apr. 2005 DOI: 10.1007/s11306-005-4810-1, pp. 101-108.

Schmitt et al., "Effects of antipsychotic treatment on membrane phospholipid metabolism in schizophrenia" *J Neural Transm* (2001) 108:1081-1091.

Shiwaku et al., "Triglyceride levels are ethnic-specifically associated with an index of stearoyl-CoA desaturase activity and n-3 PUFA levels in Asians", *Journal of Lipid Research*, vol. 45, 2004, pp. 914-922.

Wang et al., "Plasma Phospholipid Metabolic Profiling and Biomarkers of Type 2 Diabetes Mellitus Based on High-Performance Liquid Chromatography/Electrospray Mass Spectrometry and Multivariate Statistical Analysis" *Analytical Chemistry*, vol. 77, No. 13, Jul. 1, 2005 (pp. 4105-4116).

Warensjo et al., "Fatty acid composition and estimated desaturase activities are associated with obesity and lifestyle variables in men and women" *Nutrition, Metabolism & Cardiovascular Diseases* (2006) 16, 128-136.

Watkins et al. "Lipid metabolome-wide effects of the PPARγ agonis rosiglitazone" *Journal of Lipid Research*, vol. 43, 2002, pp. 1809-1817.

Watkins et al., "Metabolomics and biochemical profiling in drug discovery and development", *Current Opinion in Molecular Therapeutics* (2002) 4(3):224-228 @ PharmaPress Ltd ISSN 1464-8431.

Watkins, "Lipomic profiling in drug discovery, development and clinical trial evaluation", *Current Opinion in Drug Discovery & Development*, 2004 7(1):112-117, Thomson Scientific ISSN 1367-6733.

Watson et al., "Lipidomics: A Global Approach to Lipid Analysis in Biological Systems", *Journal of Research ASBMB*, Downloaded from www.jlr.org at Duke Medical Library, on Feb. 15, 2011, pp. 1-47.

Yao et al., "Correlations between Peripheral Polyunsaturated Fatty Acid Content and in Vivo Membrane Phospholipid Metabolites", *Biol Psychiatry* 2002;52:823-830.

Yao et al., "Membrane phospholipid abnormalities in postmortem brains from schizophrenic patients", *Schizophrenia Research* 42 (2000) 7-17.

Yao et al., "Metabolic Investigation in Psychiatric Disorders", *Molecular Neurobiology*, vol. 31, 2004, pp. 193-203.

Yao et al., "Red blood cell membrane dynamics in schizophrenia. II. Fatty acid composition", *Schizophrenia Research*, 13 (1994) 217-226.

Boston et al. "Serum Cholesterol and Treatment-Resistance in Schizophrenia," *Biol Psychiatry* 1996;40:542-543.

Papakostas et al. "Serum Cholesterol in Treatment-Resistant Depression," *Neuropsychobiology* 2003;47:146-151.

\* cited by examiner

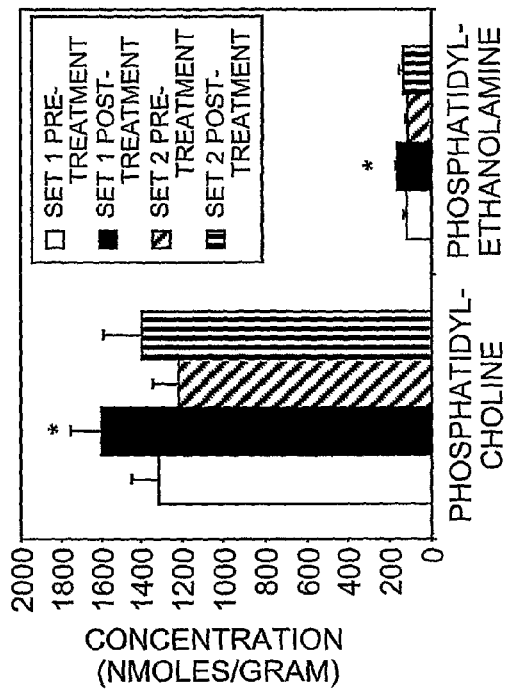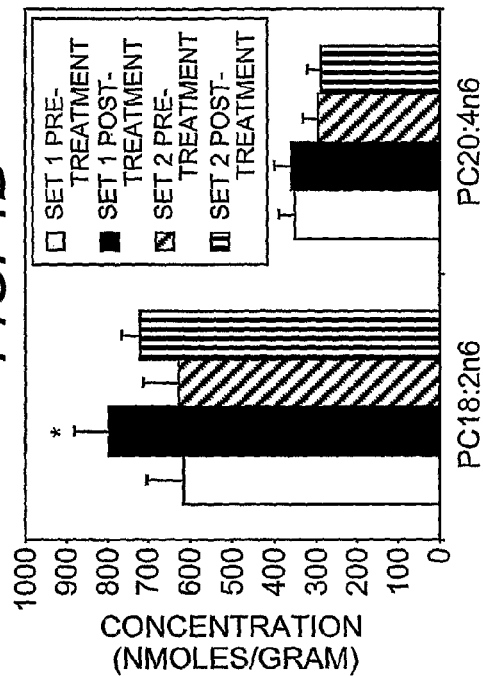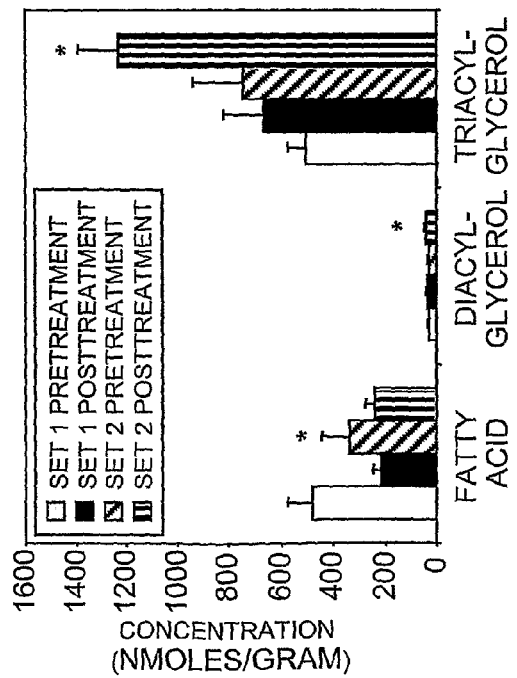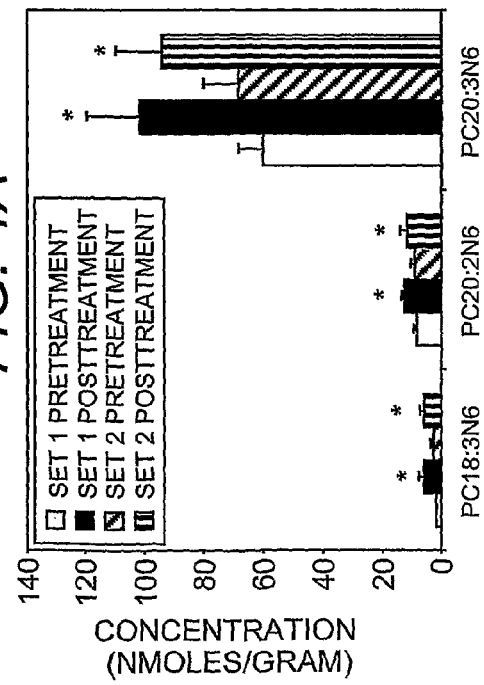

LIPIDOMICS APPROACHES FOR CENTRAL NERVOUS SYSTEM DISORDERS

CROSS-REFERENCE TO RELATED APPLICATIONS

This application is a 35 U.S.C. §371 national phase application of International Application Serial No. PCT/US2006/040026; filed Oct. 12, 2006, which claims priority to U.S. Provisional Application No. 60/729,664, filed Oct. 24, 2005, and U.S. Provisional Application No. 60/794,691, filed Apr. 24, 2006, the disclosures of which are incorporated herein by reference in their entireties.

RELATED APPLICATION INFORMATION

This application claims the benefit of U.S. Provisional Application Ser. No. 60/729,664 filed Oct. 24, 2005 and U.S. Provisional Application Ser. No. 60/794,691 filed Apr. 24, 2006, the disclosures of which are incorporated herein by reference in their entireties.

FIELD OF THE INVENTION

The present invention relates to metabolomics; in particular, the present invention relates to the application of lipidomics to central nervous system disorders.

BACKGROUND OF THE INVENTION

Schizophrenia is a debilitating mental disorder characterized by psychosis, negative symptoms and neurocognitive deficits (Jablensky et al., (1992) *Psychol. Med. Monogr Suppl.* 20:1-97). Theories of the pathophysiology underlying schizophrenia have centered on neurotransmitters and their receptors and therapeutic drug development has largely targeted dopamine, serotonin and glutamate systems (Javitt D C, Laruelle M. Neurochemical theories. In: Lieberman J A, Stroup T S, Perkins D O, eds. Textbook of Schizophrenia. Washington D.C.: American Psychiatric Publishing; 2006: 85-116; Meltzer, 9187) *Schizophr. Bull.* 13:77-111; Scolnick, (2006) *Biol. Psychiatry* 59:1039-45). While such therapies have proven effective in short-term trials, the vast majority of individuals discontinue treatment over time for lack of effectiveness or development of side effects and not all patients respond similarly to these medications (Strauss et al., (1977) *Arch. Gen. Psychiatry* 34:159-63; Kane et al., (1993) *Schizophr. Bull.* 19:287-302; Carpenter et al., (1994) *N. Engl. J. Med.* 330:681-690; Lieberman et al., (2005) *N. Engl. J. Med.* 353:1209-23).

In addition, recent studies have highlighted a growing concern over the potential for antipsychotic drugs, especially clozapine and olanzapine, to cause metabolic adverse effects such as weight gain, hyperglycemia, and hypertriglyceridemia (American Diabetes Association APA, American Association of Clinical Endocrinologists, North American Association for the Study of Obesity. Consensus Development Conference on Antipsychotic Drugs and Obesity and Diabetes, (2004) *J. Clin. Psychiatry* 65:267-72). For example, a 26-week randomized trial of 317 schizophrenic patients found that patients randomized to olanzapine were more likely to develop weight gain and total cholesterol/triglyceride elevations than those randomized to aripiprazole (McQuade et al., (2004) *J. Clin. Psychiatry* 65 Suppl. 18:47-56). However, to date no study has done comprehensive analyses of global lipid effects of various atypical antipsychotics.

The development of antipsychotic drugs in the 1950s, and the pioneering work of Arvid Carlsson, led to the subsequent advancement of the dopamine hypothesis of schizophrenia. The elucidation of dopamine pathways in the CNS, and the subsequent identification of dopamine antagonism as the common mechanism of action for typical antipsychotic medications, permitted the development of dozens of active molecules for the treatment of schizophrenia. The strength of the dopamine hypothesis is that it explains why, to date, no effective antipsychotic medication has been developed which does not, in some way, modulate dopamine neurotransmission. The limitations are clear, and relate to the large body of evidence that implicates other developmental processes and receptor pathways in the pathogenesis and manifestations of schizophrenia including other receptors such as serotonin and glutamate.

The synthesis of antipsychotic medications resulted in dramatic improvements for many sufferers of schizophrenia, and allowed many to resume life in the community. While the conventional antipsychotic drugs, such as the phenothiazines and haloperidol, are often effective in the treatment of the positive symptoms of schizophrenia, they offer little or no control of negative symptoms, and do not usually improve the cognitive deficits associated with schizophrenia, and may even exacerbate them. The conventional antipsychotic drugs are all potent dopamine D2 antagonists, and suffer from a very narrow therapeutic index whereby doses sufficient to control symptoms often result in the development of adverse reactions such as extrapyramidal effects (EPS) (e.g., parkinsonism), and a 4-5% annual incidence of tardive dyskinesia.

The newer generation of antipsychotics, often referred to as atypicals, offer two major advantages. Firstly, they are characterized by a much broader separation between the doses required for therapeutic response and those that induce extrapyramidal side effects. In addition, and to varying extents, the new drugs can improve the negative as well as the positive symptoms of schizophrenia. They also appear to offer some improvement in schizophrenia-associated cognitive deficits. Both the expanded therapeutic index and the lowered tendency to induce EPS are thought to depend on the fact that the atypicals are weaker antagonists of dopamine D2 receptors than typicals, but are potent antagonists of serotonin 5-HT2 receptors.

Despite the clear benefits of atypicals, however, many patients continue to suffer to some degree from a lack of control of negative symptoms, and from cognitive impairments. In addition, the atypical antipsychotics may cause serious metabolic side effects such as weight gain, hyperlipidemia and glycemic complications. Some of the atypicals, particularly risperidone, also carry a risk of EPS and hyperprolactinemia, albeit usually lower than for conventional antipsychotics. In addition, some patients, classified as "treatment resistant," do not respond to any existing antipsychotic drugs. This population has been estimated to be as high as 30% of schizophrenia patients, and represents a major unmet clinical need.

While schizophrenia is associated with psychosis, emotional and cognitive dysfunction, one important clinical feature of schizophrenia is the greater risk than other members of society for developing obesity and metabolic disorders such as type 2 diabetes mellitus (DM) and the metabolic syndrome. This high prevalence of metabolic dysfunction is thought to be related to many factors including possible inherent vulnerability, inactive lifestyle, poor dietary choices, and side effects of psychotropic medications. Diabetes mellitus in particular has received significant attention in the schizophrenia literature over the past 5 years for several reasons: a) recent data confirming that DM is twice as prevalent among schizophrenia cohorts than in the general population; b) the concern about glucose intolerance, DM and diabetic ketoacidosis associated with atypical antipsychotic therapy culminating in FDA warnings and the recent American Diabetes Association/American Psychiatric Association (ADA/APA) Consensus paper on this topic (American Diabetes Association, A.P.A., American Association of Clinical Endocrinologists, North American Association for the Study of Obesity, *Consensus Development Conference on Antipsychotic Drugs and Obesity and Diabetes*, J. Clin. Psychiatry 65: 267-272 (2004); and c) changes in the third revision of the National Cholesterol Education Program's Adult Treatment Protocol (AT-PIII) which elevated DM to a disorder considered equivalent in 10-year risk for a major cardiovascular event to established coronary heart disease (CHD).

It is hypothesized that a predilection towards abdominal or visceral adiposity places schizophrenia patients at risk for development of the metabolic syndrome, and eventually for type 2 DM through the correlation with decreased insulin sensitivity.

There may be several factors underlying the observation that patients with schizophrenia are at risk for the metabolic syndrome. Aside from a predisposition towards central obesity, environmental factors such as diet, inactivity, and the contributions of atypical antipsychotics play a significant role. The ADA/APA Consensus paper recognized that certain atypical antipsychotics are associated with greater metabolic dysfunction than others, including weight gain, hypertriglyceridemia, and risk of new onset DM or hyperglycemia. Prospective data on weight gain show mean increases during the first year of therapy of 11.7-13.9 lbs for clozapine, and 15.0-26.0 lbs for olanzapine, while risperidone and quetiapine reported mean gains of 4.4-5.1 lbs and 6.1-12.3 lbs respectively, and ziprasidone and aripiprazole<2 lbs. Multiple sources of data also reveal that treatment with clozapine or olanzapine is associated with increases in serum triglycerides over the first year of treatment ranging from 50 to over 100 mg/dl with serum levels over 7000 mg/dl reported, while aripiprazole and ziprasidone appear lipid-neutral, and discrepant data exist on risperidone and quetiapine. Although patients with schizophrenia have a vulnerability towards DM which places them at risk for this outcome even with metabolically neutral agents such as haloperidol, the accumulated body of evidence points towards clozapine and olanzapine as agents associated with higher risk, while ziprasidone and aripiprazole appear to have minimal effects on serum glucose.

SUMMARY OF THE INVENTION

Metabolomics is the study of metabolism at the global level. It involves systematic study of the metabolome, the complete repertoire of small molecules present in cells, tissues or organisms. Sophisticated metabolomic analytical platforms and informatics tools have already been developed that are making it possible to begin the process of defining signatures for disease and pathways implicated in disease process (Brindle et al., *Nature Med.* (2002) δ: 1439-44; Brindle et al., (2003) *Analyst* 128:32-36; Rozen et al., (2005) *Metabolomics* 1:101-108; Dunne et al., (2005) *NMR Biomed.* 18:24-33; Kenny et al., (2005) *Metabolomics* 1:277; Wang et al., (2005) *Anal. Chem.* 77:4108-4116; Yang et al., (2004) *J. Chromatogr. B Analyst Technol. Biomed. Life Sci.* 813: 59-65; Odunsi et al., (2005) *Int J. Cancer* 113: 782-788). Lipidomics is a branch of metabolomics where the focus is specifically targeted on evaluating a wide range of lipid metabolites enabling a more comprehensive assessment of human lipid biochemical pathways than was previously practical (Watkins et al., (2002) *J. Lipid Res.* 43:1809-17; Watkins et al., (2004) *Curr Opin. Drug Discov Devel.* 7:112-117; Watson, Lipidomics: A global approach to lipid analysis in biological systems. *J. Lipid Res.* Aug. 10, 2006 [Epub ahead of print]).

The present invention has utilized the power of lipidomics to profile lipids and to characterize changes in lipid metabolism as they relate to central nervous system (CNS) disorders. Lipidomics technology is a powerful tool that enables the interrogation of lipid biochemistry at a global level. Lipidomic signatures can guide the development of diagnostic, prognostic and surrogate markers for CNS disorders; identification of new targets for drug design based on highlighted perturbed pathways; stratify patients with CNS disorders as to which pathways are impaired, and facilitate the determination of which patients with CNS disorders are candidates for a particular therapy, i.e. provide the tools for a personalized approach to therapy; enable the design of modified antipsychotics that have less metabolic side effects and enhanced activity; overcome the lag phase in response to some treatments; and find better combination therapies for CNS disorders that target the pathways that are impaired (e.g., impairments in lipid and/or carbohydrate metabolism).

The inventors have compared the lipid metabolome of schizophrenic patients who are drug free to that of age and gender matched healthy controls. Sophisticated mathematical tools enabled derivation of an initial lipid metabolic signature (i.e., before treatment) for the disease. Additionally, the inventors have determined metabolic signatures in schizophrenic patients on one of several antipsychotic drugs (risperidone, olanzapine or aripiprazole) used for the treatment of the disease. Lipidomic analysis has highlighted pathways implicated in the mechanism of action of these drugs and cellular targets that may be involved in the development of metabolic side effects.

Schizophrenia is a devastating disease with socioeconomic impact. Causes are not known and therapies are not optimal. Most antipsychotics are only partially effective and metabolic side effects are major issues for schizophrenia patients where weight gain, high triglycerides and insulin resistance may occur resulting in the metabolic syndrome. Moreover, it is not clear if the metabolic side effects of the antipsychotics are related to the mechanism of action. Lipidomics provides a powerful new approach with promise to derive global lipid biochemical changes in schizophrenia and to establish characteristic and unique metabolic patterns for the disease and its different phenotypic forms. These signatures and knowledge of the corresponding molecular structures provide diagnostic markers for the disease and provide insights into disease mechanism. Signature biomarkers for schizophrenia are valuable because they may point to new hypotheses in the pathogenesis, and may serve as surrogate indices of disease activity that enhance monitoring for therapeutic effect.

Additionally, the metabolic signatures of antipsychotic drugs can highlight networks and pathways implicated in their mode of action. This can result in better design of antipsychotics that have less side effects and better efficacy than what is currently available. Further, these studies can identify sub signatures in schizophrenia that correlate with different phenotypes of the disease and response to therapy. Definition of subpopulations in schizophrenia permits a more personalized approach to the treatment of the disease.

Accordingly, as one aspect the invention provides a method of correlating a lipid profile with the presence of a central nervous system (CNS) disorder in a mammalian subject, the method comprising:

obtaining a lipid profile of a sample from a subject with the CNS disorder; and correlating the lipid profile with the presence of the CNS disorder.

As another aspect the invention provides a method of determining if a mammalian subject has a central nervous system (CNS) disorder, the method comprising:

correlating a lipid profile with the presence of the CNS disorder; and obtaining a lipid profile of a sample from the subject, wherein the lipid profile in the sample indicates whether the subject has the CNS disorder.

The invention further provides a method of determining if a mammalian subject has a central nervous system (CNS) disorder, the method comprising:

obtaining a lipid profile of a sample from the subject, wherein the lipid profile in the sample as compared with a standard lipid profile in a mammalian subject without the CNS disorder indicates whether the subject has the CNS disorder.

As yet another aspect, the invention provides a method of correlating a lipid profile with the risk of developing a CNS disorder in a mammalian subject, the method comprising:

obtaining a lipid profile of a sample from a subject at risk for the central nervous system (CNS) disorder; and correlating the lipid profile with the risk of developing the CNS disorder.

The invention further provides, a method of determining if a mammalian subject is at risk for a central nervous system (CNS) disorder, the method comprising:

correlating a lipid profile with the risk of developing the CNS disorder; and obtaining a lipid profile of a sample from the subject, wherein the lipid profile in the sample indicates whether the subject is at risk for the CNS disorder.

As another aspect, the invention provides a method of determining if a mammalian subject is at risk for a central nervous system (CNS) disorder, the method comprising:

obtaining a lipid profile of a sample from the subject, wherein the lipid profile in the sample as compared with a standard lipid profile in a mammalian subject that is not at risk for the CNS disorder indicates whether the subject is at risk for the CNS disorder.

As still another aspect, the invention provides a method of correlating a lipid profile with the progression of a central nervous system (CNS) disorder in a mammalian subject, the method comprising:

obtaining a lipid profile of a sample from a subject with the CNS disorder; and correlating a change in the lipid profile over time with the progression of the CNS disorder.

Still further, the invention provides a method of monitoring the progression of a central nervous system (CNS) disorder in a mammalian subject, the method comprising:

correlating a lipid profile with the progression of the CNS disorder;

obtaining a lipid profile of a sample from the subject; and monitoring changes in the lipid profile in the subject over time, thereby monitoring the progression of the CNS disorder.

The invention also provides a method of monitoring the progression of a central nervous system (CNS) disorder in a mammalian subject, the method comprising:

obtaining a lipid profile of a sample from the subject, wherein the lipid profile is correlated with the progression of the CNS disorder; and monitoring changes in the lipid profile in the subject over time, thereby monitoring the progression of the CNS disorder.

As still a further aspect, the invention provides a method of correlating a lipid profile with a prognosis for the course of a central nervous system (CNS) disorder in a mammalian subject, the method comprising:

obtaining a lipid profile of a sample from a subject with the CNS disorder; and correlating the lipid profile in the sample with the prognosis for the course of the CNS disorder in the subject.

The invention also provides a method of determining a prognosis for the course of a central nervous system (CNS) disorder in a mammalian subject, the method comprising:

correlating a lipid profile with the course of the CNS disorder; and obtaining a lipid profile of a sample from the subject, wherein the lipid profile in the sample indicates the prognosis for the course of the CNS disorder in the subject.

In some embodiments, the invention provides a method of determining a prognosis for the course of a central nervous system (CNS) disorder in a mammalian subject, the method comprising:

obtaining a lipid profile of a sample from the subject, wherein the lipid profile is correlated with the prognosis for the course of the CNS disorder; and determining the prognosis for the course of the CNS disorder in the subject.

In some aspects, the invention provides a method of correlating a lipid profile with an effective treatment regimen for a central nervous system (CNS) disorder, the method comprising:

obtaining a lipid profile of a sample prior to treatment from a mammalian subject with the CNS disorder; and correlating the lipid profile in the sample with a treatment regimen that is effective for treating the CNS disorder.

The invention also provides a method of determining whether a treatment regimen is effective for treating a mammalian subject with a central nervous system (CNS) disorder, the method comprising:

correlating a lipid profile prior to treatment with an effective treatment regimen for the CNS disorder; and obtaining a lipid profile of a sample from the subject prior to treatment, wherein the lipid profile in the sample indicates whether the treatment regimen is effective for treating the CNS disorder in the subject.

In yet further embodiments, the invention provides a method of determining whether a treatment regimen is effective for treating a mammalian subject with a central nervous system (CNS) disorder, the method comprising:

obtaining a lipid profile of a sample from the subject prior to treatment, wherein the lipid profile in the sample correlates with an effective treatment regimen for the CNS disorder; and determining whether the treatment regimen is effective for the subject.

In further aspects, the invention provides a method of correlating a lipid profile with a positive or negative response to a treatment regimen and/or with a side effect to the treatment regimen for a central nervous system (CNS) disorder, the method comprising:

obtaining a lipid profile of a sample from a mammalian subject with the CNS disorder following commencement of the treatment regimen;

correlating the lipid profile in the sample with a positive or negative response and/or with a side effect to the treatment regimen.

As still another aspect, the invention provides a method of determining a positive or negative response to a treatment regimen and/or a side effect to a treatment regimen by a mammalian subject with a central nervous system (CNS) disorder, the method comprising:

correlating a lipid profile with a positive or negative response/or a side effect to the treatment regimen; and detecting a lipid profile of a sample from the subject, wherein the lipid profile in the sample indicates whether the subject is responding positively or negatively to the treatment regimen and/or is developing a side effect from the treatment regimen.

These and other aspects of the invention are set forth in more detail in the following description of the invention.

BRIEF DESCRIPTION OF THE DRAWINGS

FIG. 1C shows the most significantly modified lipid metabolites in plasma of patients treated with olanzapine and highlights which of these metabolites are also modified upon treatment with risperidone or aripiprazole. The column headers indicate fatty acid metabolites as they appear in each distinct lipid class (rows). In FIG. 1A, lipids whose percent levels were higher or lower in patients vs. controls are as indicated by the scale; see Examples for details. In (FIG. 1B) to (FIG. 1C), the percent increase in any lipid upon treatment with drug is as indicated by the scale and is described in the Examples. Squares with "+" indicate an increase and squares with "−" indicate a decrease. Unlabeled squares were unchanged. The brightness of each square corresponded to the magnitude of the difference in quartiles. The brighter the square, the larger the difference.

FIGS. 4A to 4H. Comparisons of risperidone (FIG. 4A to FIG. 4D), olanzapine (FIG. 4E and FIG. 4F), and aripiprazole (FIG. 4G and FIG. 4H) drug effects on plasma lipid subclasses and fatty acids between the 1st and 2nd set of patients with schizophrenia.

DETAILED DESCRIPTION OF THE INVENTION

Figure 1A:
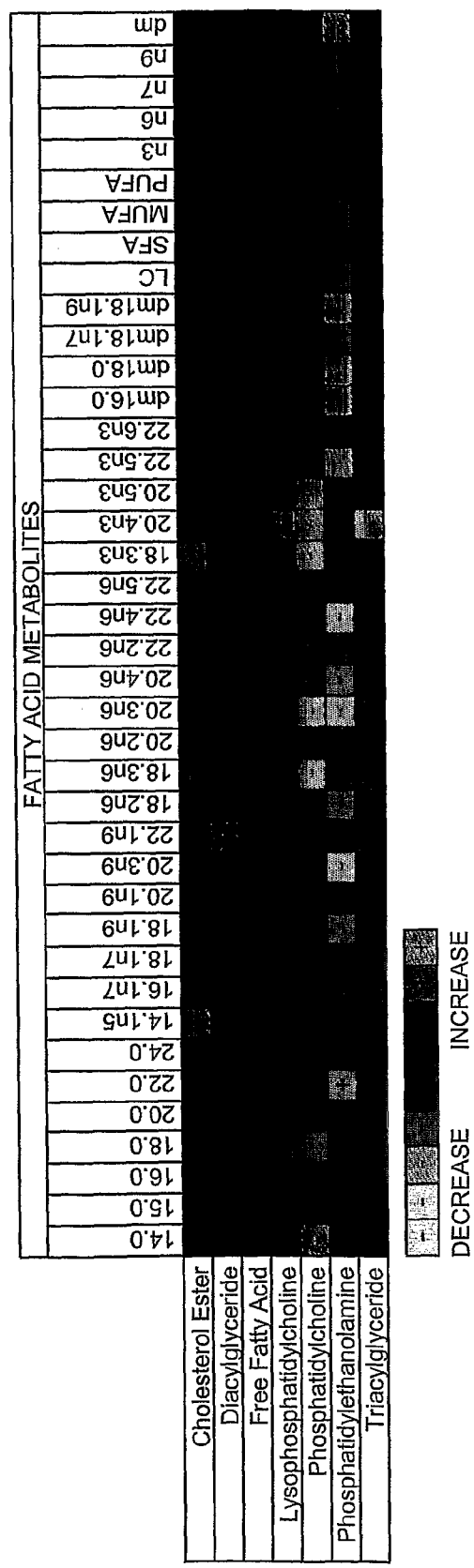
FIGS. 1A to 1C. Heat map showing differences in individual lipid metabolites in the plasma of patients with schizophrenia as compared with controls (FIG. 1A) or in the plasma of schizophrenic patients post-treatment as compared with pre-treatment (FIG. 1B) with olanzapine, risperidone, and aripiprazole.

Metabolomics, the study of metabolism at the global or "-omics" level, is a new but rapidly growing field with the potential to impact the practice of medicine at many levels. Metabolomics studies the metabolome, the repertoire of small molecules present in cells and tissue. The identities, concentrations, and fluxes of these substances are the final product of interactions between gene expression, protein expression, and the cellular environment.

Many diseases disrupt metabolism and result in changes that are long lasting and that can be captured as metabolic signatures. Using the 1H-NMR-based metabolomics approach (Brindle et al., (2003) *Analyst* 128:32-6), a rapid and noninvasive diagnosis for the presence and severity of coronary heart disease was established. A class of lipid metabolites contributed to the separation of coronary heart disease patients from controls. Using an electrochemical metabolomics platform (Rozen et al., (2005) *Metabolomics* 1:101-108), metabolic signatures for motor neuron diseases have been identified. These metabolic signatures represent tens of metabolites that are deregulated (up and down) in the disease state and provide information about the disease process. The present invention has broad applications in research and medical practice that include: (i) development of prognostic, diagnostic and surrogate markers of a disease state; (ii) novel ability to sub-classify diseases; (iii) better design of clinical trials based on sub-classification of patients and early monitoring of drug effects; (iv) individualized therapy where the right drug is delivered to the right patient (pharmacometabolomics); (v) information about mechanisms of disease; (vi) early mapping of the beneficial and side effects of drugs; and (vii) characterization of healthy individuals.

The present invention is based in part on a lipidomics approach to central nervous system (CNS) disorders, for example, to identify diagnostic, prognostic and surrogate signatures for CNS disorders, including subsignatures to stratify different populations of subjects, to provide more personalized therapy (pharmacometabolomics), and to highlight the pathways that are perturbed in response to disease or therapy for the disease. Highlighted pathways provide new targets for drug design and facilitate combination therapies to treat the side effects associated with CNS disorders and drug therapies.

The present invention greatly expands the repertoire of diagnostic, prognostic and pharmacometabolomics tools for CNS disorders by providing diagnostic signatures for disease, and subsignatures to identify different populations of diseased individuals, prognostic signatures of CNS disorders, surrogate markers for CNS disorders, and lipid maps for monitoring the response to therapy, to identify those patients at risk for developing side effects in response to therapy, and to proactively identify which patients are good candidates for a particular therapy.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

The terminology used in the description of the invention herein is for the purpose of describing particular embodiments only and is not intended to be limiting of the invention.

As used herein, the singular forms "a," "an" and "the" are intended to include the plural forms as well, unless the context clearly indicates otherwise.

As used herein, "and/or" refers to and encompasses any and all possible combinations of one or more of the associated listed items.

Moreover, the present invention also contemplates that in some embodiments of the invention, any feature or combination of features specifically set forth herein can be excluded or omitted.

Those skilled in the art will appreciate that all of the methods of the invention of the present invention can be practiced with any combination of the features described herein, including but not limited to: subject, sample, CNS disorder, and component(s) of the lipid profile, the latter including without limitation the classes and subclasses of lipids evaluated in the profile, and the manner in which they are evaluated (e.g., methodology used and method of expressing the results [for example, as an absolute amount such as weight or moles or a relative amount such as a weight %, mole % or ratio]).

The following abbreviations are used herein:
CE=cholesterol ester
DAG=diacylglycerol
DG=diacylglycerols
dm=plasmalogen linked fatty acids
FA=free fatty acid
FC=free cholesterol
LC=total lipid class
LY=lysophosphatidylcholine
LYPC=lysophosphatidylcholine
MAG=monoacylglycerol
MUFA=mono unsaturated fatty acid
PA=phosphatidic acid
PC=phosphatidylcholine
PE=phosphatidylethanolamine
PG=phosphatidylglycerol
PI=phosphatidylinositol
PL=phospholipids
PS=phosphatidylserine
PUFA=polyunsaturated fatty acid
SAT=saturated fatty acid
SFA=saturated fatty acid
SM=sphingomyelin
SP=sphingmyelin
t=trans
TAG=triacylglycerol
TG=triacylglycerol
n3=fatty acids with n3 double bonds
n6=fatty acids with n6 double bonds
n7=fatty acids with n7 double bonds
n9=fatty acids with n9 double bonds Phospholipids are formed from four components: a backbone to which is linked two fatty acid-derived "tails" by ester linkages and one "head" group by a phosphate ester, and an alcohol. Phospholipids with a glycerol backbone are known as glycerophospholipids or phosphoglycerides. Sphingomyelin is a phospholipid with a sphingosine backbone. Phospholipids are a major component of all biological membranes, along with glycolipids and cholesterol. The head groups of the phospholipids found in biological membranes are phosphatidylcholine (lecithin), lysophosphatidyl choline, phosphatidylethanolamine, phosphatidylserine and phosphatidylinositol, whose head group can be modified by the addition of one to three more phosphate groups. While phospholipids are the major component of biological membranes, other lipid components like sphingolipids and sterols (such as cholesterol in animal cell membranes) are also found in biological membranes.

Cardiolipin (diphosphatidyl glycerol) is an important component of the mitochondrial membrane, typically present in metabolically active cells of the heart and skeletal muscle. It has also been observed in certain bacterial membranes. It serves as an insulator and stabilizes the activity of protein complexes important to the electron transport chain.

Fatty acids are unbranched hydrocarbon chains, connected by single bonds alone (saturated fatty acids) or by both single and double bonds (unsaturated fatty acids). Examples of saturated fatty acids include but are not limited to butyric acid, lauric acid, myristic acid, pentadecanoic acid, palmitic acid, stearic acid, arachidic acid, behenic acid and lignoceric acid. Examples of unsaturated fatty acids include but are not limited to linolenic acid, docosahexaenoic acid, eicosapentaenoic acid, linoleic acid, arachidonic acid, oleic acid, and erucic acid. Particular classes of fatty acids include omega-3 fatty acids (e.g., alpha-linolenic, stearidonic, eicosatrienoic, eicosatetraenoic, eicosapentaenoic, docosapentaenoic, docosahexaenoic and tetracosahexaenoic acids), omega-6 fatty acids (e.g., linoleic, gamma-linolenic, eicosadienoic, homo-gamma-linolenic, arachidonic, docosadienoic, docosatetraenoic and 4,7,10,13,16-docosapentaenoic acids) and omega-9 fatty acids (e.g., myristoleic, palmitoleic, vaccenic, oleic, eicosenoic, mead, erucic and nervonic acids). Other fatty acids include plasmalogen-linked fatty acids including but not limited to plasmalogen 16:0, plasmalogen 18:0, plasmalogen 18:1n7 and plasmalogen 18:1n9. Other fatty acids include but are not limited to palmitelaidic acid, elaidic acid, 8-eicosaenoic acid and 5-eicosaenoic acid.

Essential fatty acids include the polyunsaturated fatty acids, linoleic acid and alpha-linolenic acid, which are the parent compounds of the omega-6 and omega-3 fatty acid series, respectively. They are essential in the human diet since they cannot be synthesized by the body, as the enzymes to introduce a double bond at the omega-3 and omega-6 positions are absent. The essential fatty acids are important for the immune system and in blood pressure regulation, since they are used to make compounds such as prostaglandins. The brain is also highly enriched in derivatives of linolenic and linoleic acids.

The foregoing discussion applies to free fatty acids and to fatty acid moieties found incorporated into lipid molecules in other classes (e.g., diglycerides, triglycerides and phospholipids).

Triglycerides (triacylglycerols) are the most abundant dietary lipids. They are the form in which reduced carbon is stored for energy. Each triacylglycerol has a glycerol backbone to which 3 fatty acids are esterified. Most triacylglycerols are "mixed" in that the three fatty acids differ in chain length and/or number of double bonds.

Lipid metabolites are identified herein by the lipid class and the fatty acid moiety. In the context of this invention, fatty acids are identified first by the number of carbons in the molecule (e.g., 20), the number of double bonds in the molecule (e.g., 4), and lastly the position of the double bonds (e.g., n6). To illustrate, PC20:4n6 denotes a phosphatidylcholine molecule containing a 20 carbon fatty acid with 4 double bonds at the n6 position.

A "lipid metabolite" as used herein can refer to a single species within a lipid class (e.g., PC20:4n6), a subset of species within a lipid class (e.g., PCn6 or PCMUFA) or the entire lipid class (e.g., Total PE).

As used herein, the term "central nervous system disorder" is to be broadly construed and includes but is not limited to psychiatric disorders and neurodegenerative disorders. CNS disorders include but are not limited to disorders of thinking and cognition such as schizophrenia and delirium; amnestic disorders; disorders of mood, such as affective disorders and anxiety disorders (including post-traumatic stress disorder, separation anxiety disorder, selective mutism, reactive attachment disorder, stereotypic movement disorder, panic disorders, agoraphobia, specific phobias, social phobia, obsessive-compulsive disorder, acute stress disorder, generalized anxiety disorder, substance-induced anxiety disorder and/or anxiety disorder not otherwise specified); disorders of social behavior; disorders of learning and memory, such as learning disorders (e.g., dyslexia); motor skills disorders; communication disorders (e.g., stuttering); pervasive developmental disorders (e.g., autistic disorder, Rett's disorder, childhood disintegrative disorder, Asperger's disorder, and/or pervasive developmental disorder not otherwise specified) and dementia. Accordingly, the term "central nervous system disorder" encompasses the disorders listed above as well as depressive disorders (including major depressive disorder, dysthmyic disorder, depressive disorder not otherwise specified, post-partum depression); seasonal affective disorder; mania; bipolar disorders (including bipolar I disorder, bipolar II disorder, cyclothymic disorder, bipolar disorder not otherwise specified); attention-deficit and disruptive behavior disorders (including attention deficit disorder with hyperactivity disorder, conduct disorder, oppositional defiant disorder and/or disruptive behavior disorder not otherwise specified); drug addiction/substance abuse (including abuse of opiates, amphetamines, alcohol, hallucinogens, cannabis, inhalants, phencyclidine, sedatives, hypnotics, anxyolytics and/or cocaine); alcohol-induced disorders; amphetamine-induced disorders; caffeine-induced disorders; cannabis-induced disorders; cocaine-induced disorders; hallucinogen-induced disorders; inhalant-induced disorders; nicotine-induced disorders; opioid-induced disorders; phencyclidine-induced disorders; sedative, hypnotic or anxyolytic-induced disorders; agitation; apathy; psychoses; irritability; disinhibition; schizophreniform disorder; schizoaffective disorder; delusional disorder; brief psychotic disorder, shared psychotic disorder; substance-induced psychotic disorder; psychotic disorder not otherwise specified; unipolar disorders, mood disorders (e.g., mood disorder with psychotic features); somatoform disorders; factitious disorders; disassociative disorders; mental retardation; feeding and eating disorders of infancy or early childhood; eating disorders such as anorexia nervosa, bulimia nervosa and/or eating disorder not otherwise specified; sleeping disorders (e.g., dyssomnias such as primary insomnia, primary hypersomnia, narcolepsy, breathing-related sleep disorder and circadian rhythm sleep disorder and/or parasomnias); impulse control disorders (e.g., kleptomania, pyromania, trichotillomania, pathological gambling and/or intermittent explosive disorder); adjustment disorders; personality disorders (e.g., paranoid personality disorder, schizoid personality disorder, schizotypal personality disorder, antisocial personality disorder, borderline personality disorder, histrionic personality disorder, narcissistic personality disorder, avoidant personality disorder, dependent personality disorder and/or obsessive-compulsive personality disorder); Tic disorders (e.g., Tourette's disorder, chronic motor or vocal tic disorder, transient tic disorder and/or tic disorder not otherwise specified); elimination disorders; and any combination of the foregoing as well as any other disorder or group of disorders described in the Diagnostic and Statistical Manual of Mental Disorders—Fourth Edition (DSM-IV; the American Psychiatric Association, Washington D.C., 1994). "Central Nervous System disorders" also include other conditions that implicate the central nervous system including but not limited to neurodegenerative disorders such as Alzheimer's disease, involuntary movement disorders such as Parkinson's disease, Huntington's disease, amyotrophic lateral sclerosis (ALS), and the like. Other central nervous system disorders include without limitation epilepsy, multiple sclerosis, neurogenic pain, psychogenic pain, and migraines. In particular embodiments, the neuropsychiatric disorder is schizophrenia (including any one or more subtypes thereof). In other embodiments, the central nervous system disorder encompasses any subset of the foregoing diseases or excludes any one or more of the foregoing conditions. In particular embodiments, the term "central nervous system disorder" does not encompass benign and/or malignant tumors of the central nervous system.

Schizophrenia is a life-long illness with multiple features that are defined by DSM-IV criteria and are often accompanied by additional clinical features including but not limited to increased ventricle size of the brain, thinning of the cortical grey matter, and cognitive decline. The primary symptoms of schizophrenia can generally be grouped into three classifications: positive, or expressive symptomatology; negative, or deficit, symptomatology; and disorganized symptomatology as further defined in the DSM-IV.

Schizophrenia can also be subdivided into different subtypes defined according to the most significant and predominant characteristics present in each person at each point in time (e.g., paranoid type, disorganized type, catatonic type, undifferentiated type and residual type). For example, the paranoid subtype is distinguished by the presence of auditory hallucinations or prominent delusional thoughts about persecution or conspiracy, whereas the disorganized subtype is identified by disorganization of thought processes. In contrast, individuals with the catatonic subtype exhibit predominant clinical symptoms involving disturbances in movement such as a dramatic reduction in activity, to the point that voluntary movement stops, as in catatonic stupor. The undifferentiated subtype of schizophrenia is diagnosed when people have symptoms of schizophrenia that are not sufficiently formed or specific enough to permit classification of the illness into one of the other subtypes and the residual subtype is diagnosed when the patient no longer displays prominent symptoms. In such cases, the schizophrenic symptoms generally have lessened in severity, e.g., hallucinations, delusions or idiosyncratic behaviors may still be present, but their manifestations are significantly diminished in comparison to the acute phase of the illness.

The term "lipidomics" as used herein refers to the use of metabolomics as applied to the evaluation of lipid metabolites in biological samples. Lipid profiling generally involves an evaluation of lipid metabolites in one or more lipid classes (e.g., fatty acids, triglycerides, diglycerides, cholesterol esters, and the phospholipid classes including phosphatidylcholine, phosphatidylethanolamine, lysophosphatidylcholine, sphingomyelin, phosphatidylcholine, phosphatidylserine, phosphatidylethanolamine and cardiolipin).

As used herein, the term "lipid" is intended broadly and encompasses a diverse range of molecules that are relatively water-insoluble or nonpolar compounds of biological origin, including waxes, triglycerides, free fatty acids, diacylglycerols, fatty-acid derived phospholipids, sphingolipids, glycolipids and terpenoids, such as retinoids, cholesterol, cholesterol esters, and steroids. Some lipids are linear aliphatic molecules, while others have ring structures. Some are aromatic, while others are not.

As used herein, the term lipid "class" refers to a collection of lipid molecules that share structural and/or biochemical properties. According to the methods of the invention, lipids within any class(es) can be evaluated. Suitable lipid classes include polar and non-polar classes of lipids. Exemplary non-polar lipid classes include without limitation the free fatty acids, monoacylglycerides, diacylglycerides, triacylglycerides, sterols and/or cholesterol esters. Exemplary polar classes include without limitation the phospholipid classes such as phosphatidic acid, lysophosphatidylcholine, sphingomyelin, phosphatidylinositol, phosphatidylglycerol, phosphatidylcholine, phosphatidylserine, phosphatidylethanolamine, lysophosphatidylethalolamine, cardiolipin and/or lysocardiolipin.

The term "lipid profile" as used herein refers to the evaluation of one or more lipid metabolites within a biological sample. In particular embodiments, two or more, three or more, four or more, five or more, six or more, seven or more, eight or more, nine or more, ten or more, twelve or more, fifteen or more, twenty or more, fifty or more, 100 or more, or an even greater number of lipid metabolites are evaluated. In embodiments wherein two or more lipid metabolites are assessed, the two or more lipids can belong to the same class or can be belong to two or more, three or more, four or more, five or more, six or more, seven or more or a greater number of different lipid classes.

The lipid profile can be quantitative, semi-quantitative and/or qualitative. For example, the lipid profile can evaluate the presence or absence of a lipid, can evaluate the presence of a lipid(s) above or below a particular threshold, and/or can evaluate the relative or absolute amount of a lipid(s). In particular embodiments, a ratio among two, three, four or more lipids is determined. Changes or perturbations in lipid ratios can be advantageous in indicating where there are metabolic blocks (or releases of such blocks) or other alterations in metabolic pathways associated with disease, response to treatment, development of side effects, and the like (see, e.g., FIG. 5A and FIG. 5B). Methods of evaluating ratios of lipid precursors and products to evaluate enzyme activities and flow through metabolic pathways are known in the art (see, e.g., Attie et al., (2002) *J. Lipid Res.* 43:1899-1907 and Pan et al., (1995) *J. Clin. Invest.* 96:2802-2808).

Ratios of lipid metabolites can be used to reflect or assess changes in lipid metabolism. Generally, if the ratio is calculated from metabolites not present in the same lipid class, quantitative data are used to calculate the ratio. If the lipid metabolites reflected in the numerator and the denominator belong to the same lipid class, then relational data can be used.

In some embodiments, the level of a lipid metabolite is normalized against another lipid metabolite. For example, the ratio between two or more lipid metabolites can be normalized against an index associated with a pathway, enzymatic activity, class of metabolites, and/or status of certain metabolic activities. Alternatively the level of a lipid metabolite can be normalized against a housekeeping lipid metabolite, e.g., a lipid metabolite that is relatively stable in amount under a variety of conditions in the subject.

Quantitative metabolomic data include molar quantitative data, mass quantitative data and relational data by either moles or mass (mole % or weight %, respectively) for individual lipid metabolites or subsets of metabolites. In some embodiments, quantitative aspects of lipidomic analysis can be provided and/or improved by including one or more quantitative internal standards during the analysis, for instance, one standard for each lipid class. Internal standards are described in more detail in U.S. Patent Publication No. 2004/01434612 A1 (S. M. Watkins).

Truly quantitative data can be integrated from multiple sources (e.g., the data do not need to be generated with the same assay, in the same location and/or at the same time) into a single seamless database regardless of the number of metabolites measured in each, discrete, individual analysis.

A "change" in the level, amount, concentration, ratio and the like with respect to a lipid metabolite(s) can mean an increase or a decrease.

As used herein the term "level" is intended broadly and can mean a quantitative amount (e.g., weight or moles), a semi-quantitative amount, a relative amount (e.g., weight % or mole % within class or a ratio), a concentration, and the like.

In representative embodiments, the lipid profile provides a compositional analysis in which two or more, three or more, four or more, five or more, six or more, seven or more, eight or more, nine or more, ten or more, twelve or more, fifteen or more, twenty or more, fifty or more, one-hundred or more or a greater number of lipid metabolites are evaluated within a single class or within two or more, three or more, four or more, five or more, six or more, seven or more or a greater number of different lipid classes. Further, the lipid profile can assess two or more, three or more, four or more, five or more, six or more, seven or more or a greater number of different classes, and can evaluate two or more, three or more, four or more, five or more, six or more, seven or more, eight or more, nine or more, ten or more, twelve or more, fifteen or more, twenty or more, fifty or more, one-hundred or more or a greater number of lipid metabolites within each class. Optionally, the lipid profile provides a compositional analysis (e.g., mole percentage (%) of the lipid metabolite) within its class. For example, the lipid profile can include an evaluation (e.g., quantitation or determination of mole % within class) of two or more, three or more, four or more, five or more, six or more, seven or more, eight or more, nine or more, ten or more, twelve or more, fifteen or more, twenty or more, or a greater number of fatty acid moieties within one or more lipid classes (for example, diglyceride, triglyceride and/or phospholipid classes [e.g., lysophosphatidylcholine, sphingomyelin, phosphatidylcholine, phosphatidylserine, phosphatidylethanolamine and/or cardiolipin classes]).

Analysis of the fatty acid class or fatty acid moieties incorporated into lipids of other classes can evaluate any characteristic including but not limited to chain length, the degree of saturation/desaturation and/or the position of any double-bond(s) that are present. With respect to chain length, the lipid profile can evaluate the presence of short- (e.g., 4 to 6 carbons), medium- (e.g., 6 to 10 carbons), long- (e.g., 12 to 18 carbons) and very long- (e.g., 20, 22 or more carbons) fatty acids, optionally with a further evaluation of saturation/desaturation. For example, in some embodiments saturated fatty acids are detected. In other embodiments, mono- and/or poly- (i.e., two or more unsaturated bonds) unsaturated fatty acids are evaluated. The position of the unsaturated bond(s) can also be evaluated, for example, omega-3 (i.e., n3), omega-6 (i.e., n6) and/or omega-9 (i.e., n9) fatty acids have double-bonds in the 3, 6 or 9 position, respectively. Further, the presence of cis or trans bonds within unsaturated fatty acids can be assessed.

Those skilled in the art will appreciate that the lipid profile can evaluate any combination of the foregoing characteristics of fatty acids (e.g., ratios, chain length, saturation/desaturation and/or position of any double-bonds), whether present in free fatty acids or fatty acid moieties incorporated into larger lipid molecules in other lipid classes.

It is intended that the lipid profile can evaluate free fatty acids and fatty acid moieties that are incorporated into lipid molecules within other lipid class(es) having any combination of features described herein such as lipid class, chain length, saturation/desaturation and/or position of any double-bond(s) as if the individual species embodying the various combinations of features were each expressly set forth herein.

In particular embodiments, the lipid profile comprises an evaluation of one or more lipid metabolites within one or more phospholipid classes. Further, this evaluation can include an assessment of the fatty acid moieties in the phospholipid class(es). For example, one or more lipid metabolites comprising a saturated, mono-unsaturated and/or polyunsaturated fatty acid moiety can be evaluated in one or more phospholipid classes. The lipid profile can additionally evaluate chain length within the phospholipid metabolites in one or more phospholipid classes (e.g., to assess short-, medium, long- and/or very long-chain polyunsaturated phospholipid(s)).

Further, in some embodiments, the lipid profile comprises an evaluation of one or more phospholipid metabolites within one or more phospholipid classes comprising an omega-3, omega-6 and/or omega-9 fatty acid moiety.

As another option, the ratio of two or more phospholipid metabolites within one or more phospholipid classes can be evaluated.

In particular embodiments of the invention, the diagnostic and/or prognostic lipid profile does not include a free fatty acid metabolite (but may include a lipid metabolite that comprises a fatty acid moiety). Alternatively, in some embodiments, the diagnostic and/or prognostic lipid profile can comprise one or more free fatty acids.

As a further option, the lipid profile can evaluate specific free fatty acids pr fatty acid components within one or more lipid classes. Free fatty acids and fatty acid moieties that can be assessed in the lipid profile include but are not limited to: 14:0, 15:0, 16:0, 18:0, 20:0, 22:0, 24:0, 14:1n5, 16:1n7, 18:1n7, 18:1n9, 20:1n9, 20:3n9, 22:1n9, 24:1n9, 18:2n6, 18:3n6, 14:1n5, 20:1n15, 20:1n12, 18:3n3, 18:4n3, 20:3n3, 20:4n3, 20:5n3, 22:5n3, 22:6n3, 24:6n3, 18:2n6, 24:6n3, 18:2n6, 18:3n6, 20:2n6, 20:3n6, 20:4n6, 22:2n6, 22:4n6, 22:5n6, t16:1n7, t18:1n9, t18:2n6, dm16:0, dm18:0, dm18:1n9, dm18:1n7, total saturated fatty acids, total monounsaturated fatty acids, total polyunsaturated fatty acids, total LC fatty acids, total n3 (omega 3) fatty acids, total n6 fatty acids, total n7 fatty acids, total n9 fatty acids, and/or total dm fatty acids. An exemplary compositional analysis is shown in FIG. 1.

Further, the lipid profile can evaluate without limitation tetradecanoic acid, pentadecanoic acid, hexadecanoic acid, heptadecanoic acid, octadecanoic acid, eicosanoic acid, docosanoic acid, tetracosanoic acid, 9-tetradecenoic acid, 9-hexadecenoic acid, 11-octadecenoic acid, 9-octadecenoic acid, 11-eicosenoic acid, 5,8,11-eicosatrienoic acid, 13-docosenoic acid, 15-tetracosenoic acid, 9,12,15-octadecatrienoic acid, 6,9,12,15-octadecatetraenoic acid, 11,14,17-eicosatrienoic acid, 8,11,14,17-eicosictetraenoic acid, 5,8,11,14,17-eicosapentaenoic acid, 7,10,13,16,19-docosapentaenoic acid, 4,7,10,13,16,19-docosahexaenoic acid, 6,9,12,15,18,21-tetracoshexaenoic acid, 9,12-octadecadienoic acid, 6,9,12-octadecatrienoic acid, 11,14-eicosadienoic acid, 8,11,14-eicosatrienoic acid, 5,8,11,14-eicosicatetraenoic acid, 13,16-docsadienoic acid, 7,10,13,16-docosicatetraenoic acid, 4,7,10,13,16-docosapentaenoic acid, 9-trans-hexadecenoic acid, 9-trans-octadecenoic acid, 8-eicosaenoic acid, 5-eicosaenoic acid, plasmalogen fatty acids, 5b-cholestan-3b-ol, 5a-cholestan-3b-ol, 5-cholesten-3b-ol, 5,24-cholestadien-3b-ol, 5-cholestan-25a-methyl-3b-ol, 5-cholestan-24b-methyl-3b-ol, 5-cholesten-24b-ethyl-3b-ol, and/or 5,22-cholestadien-24b-ethyl-3b-ol, each as a free fatty acid or a fatty acid moiety incorporated into a larger lipid molecule.

Those skilled in the art will appreciate that the lipid profile can be relatively straight-forward (e.g., detecting the presence, amount and/or mole % within class) of relatively few (e.g., one, two, three or four) lipid metabolites or can be quite complex and encompass tens or even hundreds of lipid metabolites, optionally including a compositional analysis of the metabolites within one or more lipid classes. Thus, it will also be apparent that the lipid profiles and the methods described herein can be practiced to evaluate any combination of the lipid characteristics described herein.

In particular embodiments, the lipid profiles of the invention detect about 25% or more, about 40% or more, about 50% or more, about 60% or more, about 70% or more, about 75% or more, about 80% or more, about 85% or more, about 90% or more, about 95% or more, about 97% or more, about 98% or more, or about 99% or more of the lipid metabolites in a sample.

The lipid profile can be based on any suitable biological sample. The biological sample can be taken from a subject (e.g., a patient) and can be a centrally and/or peripherally derived biological sample, including without limitation body fluids, tissue, cellular, subcellular and/or extracellular biological samples. Illustrative tissues and cells include, but are not limited to, skeletal muscle tissue and cells, skin tissue and cells, neural tissue and cells including brain tissue and cells, spinal cord tissue and cells, eye tissue and cells (e.g., retinal cells), cardiac muscle tissue and cells, lung tissue and cells, pancreatic tissue and cells, liver tissue and cells, tissue and cells of the gastrointestinal system, adipose tissue and cells, and the like. Subcellular samples include one or more fractions and/or organelles of the foregoing cell types including but not limited to cytoplasm, nuclei, mitochondria, Golgi apparatus, endoplasmic reticulum, ribosomes, lysosomes, plasma membranes, endosomal traction, and the like. Examples of body fluids include but are not limited to blood, plasma, serum, saliva, urine, lymph, semen, tears and cerebrospinal fluid.

The sample can be from any suitable subject. In particular embodiments the subject is a mammalian subject, which includes but is not limited to human, non-human primate, cattle, goats, sheep, horse, pig, dog, cat, rat, mouse, or hamster subjects and can further be male and/or female subjects. Human subjects include infants, children, adolescents, adult and/or elderly subjects. In some embodiments, the subject is an animal model for a CNS disorder. In other embodiments, the subject has or is at risk for a CNS disorder. The subject might be at risk for the psychiatric disorder, for example, because of family history and/or environmental influences (including prior therapy).

The lipid profile of the biological sample can be determined using any suitable method. The different classes of lipids and methods of detecting and optionally quantifying the same are well known in the art (e.g., thin layer chromatography, gas chromatography, liquid chromatography, mass and NMR spectrometry, and any combination thereof (e.g., GC/MS), and the like). One suitable method of detecting, and optionally quantifying, lipids in a biological sample employs stable isotope tracers to label the lipids. Methods of obtaining lipid profiles from biological samples have been described, see, e.g., U.S. Patent Publication No. 2004/0143461 A1 (S. M. Watkins) and Watkins et al. (2002) *J. Lipid Res.* 43(11): 1809-17.

One approach uses the methods and analytical tools developed by Lipomics Technologies (West Sacramento, Calif.). Lipomics Technologies has developed powerful tools to track non-polar and polar lipids and map changes in disease to biochemical pathways. The Lipomics Profile provides comprehensive data on lipids present in a sample. A non-polar lipid analysis includes a complete quantification of the fatty acids from the free fatty acid, diglyceride, triglyceride, and cholesterol ester fractions of a sample. Additionally, Lipomics can determine the concentration of each fatty acid within an aggregate phospholipid fraction. A single non-polar TrueMass® analysis can produce as many as 200 individually quantified lipid metabolites. A polar lipid analysis can include a complete quantification of the fatty acids from the phospholipid classes including: lysophosphatidylcholine, sphingomyelin, phosphatidylcholine, phosphatidylserine, phosphatidylethanolamine and cardiolipin. A single polar lipid TrueMass® analysis can produce as many as 250 individually quantified lipid metabolites.

The lipidomics profile can be based on quantitative, semi-quantitative and/or qualitative analysis. For example, qualitative methods can be used to detect the presence or absence of a lipid metabolite(s) in a biological sample. Semi-quantitative quantitative methods can be used to determine a level of a particular lipid metabolite(s) above a threshold value or to determine ratios of different lipid metabolites, without assigning an absolute or relative numerical value. Quantitative methods can be used to determine a relative or absolute amount of a particular lipid metabolite(s) in the biological sample.

In semi-quantitative methods, a threshold or cutoff value can be determined by any means known in the art, and is optionally a predetermined value. In particular embodiments, the threshold value is predetermined in the sense that it is fixed, for example, based on previous experience with the assay and/or a population of affected and/or unaffected subjects. Alternatively, the term "predetermined" value can also indicate that the method of arriving at the threshold is predetermined or fixed even if the particular value varies among assays or may even be determined for every assay run.

The lipidomics analysis of the invention can generate high-density data sets that can be evaluated using informatics approaches. High data density informatics analytical methods are known and software is available to those in the art, e.g., cluster analysis (Pirouette, Informetrix), class prediction (SIMCA-P, Umetrics), principal components analysis of a computationally modeled dataset (SIMCA-P, Umetrics), 2D cluster analysis (GeneLinker Platinum, Improved Outcomes Software), and metabolic pathway analysis (biotech.icmb.utexas.edu). The choice of software packages offers specific tools for questions of interest (Kennedy et al., Solving Data Mining Problems Through Pattern Recognition. Indianapolis: Prentice Hall PTR, 1997; Golub et al., (2999) Science 286:531-7; Eriksson et al., Multi and Megavariate Analysis Principles and Applications: Umetrics, Umea, 2001). In general, any suitable mathematic analyses can be used to evaluate one, two or more lipid metabolites in a lipid profile with respect to a CNS disorder. For example, methods such as multivariate analysis of variance, multivariate regression, and/or multiple regression can be used to determine relationships between dependent variables (e.g., clinical measures) and independent variables (e.g., levels of lipid metabolites). Clustering, including both hierarchical and nonhierarchical methods, as well as nonmetric Dimensional Scaling can be used to determine associations among variables and among changes in those variables.

In addition, principal component analysis is a common way of reducing the dimension of studies, and can be used to interpret the variance-covariance structure of a data set. Principal components may be used in such applications as multiple regression and cluster analysis. Factor analysis is used to describe the covariance by constructing "hidden" variables from the observed variables. Factor analysis may be considered an extension of principal component analysis, where principal component analysis is used as parameter estimation along with the maximum likelihood method. Furthermore, simple hypothesis such as equality of two vectors of means can be tested using Hotelling's T squared statistic.

In particular embodiments, the lipidomics approach can be combined with additional metabolomics platforms that interrogate other subsets of the metabolome and/or with genomic approaches. For example, with respect to the latter, starting from the genome, if a particular gene is known to be implicated in a disease, this pathway can be evaluated using a lipidomics platform to see if metabolites associated with this pathway are perturbed. Alternatively, if lipidomics points to particular pathways and enzymes as being involved in a disorder, or in producing adverse side effects in response to particular drugs, a genomics approach can be used to see if there are impairments in the genes of susceptible individuals (e.g., SNPs).

Diagnostic and Prognostic Methods.

The present invention can be practiced in the field of predictive medicine for the purposes of diagnosis, prognosis, monitoring the course of a disease in a subject, monitoring response to therapy, monitoring the development of side effects and/or predicting efficacy and/or side effects of a particular treatment, and the like.

In some embodiments, the invention provides methods of diagnosing a CNS disorder in a subject. A "diagnostic" method, as used herein, refers to a screening procedure that is carried out to identify those subjects that are affected with a particular disorder.

In particular embodiments, the invention provides a method of correlating a lipid profile with the presence of a CNS disorder in a mammalian subject, the method comprising: (a) obtaining a lipid profile of a sample from a subject with the CNS disorder; and (b) correlating the lipid profile with the presence of the CNS disorder. For example, the lipid profile can be compared between diseased and control (e.g, healthy) subjects in order to correlate the lipid profile from diseased subjects with the presence of the CNS disorder.

In other embodiments, the invention provides a method of determining if a mammalian subject has a CNS disorder, the method comprising: (a) correlating a lipid profile with the presence of the CNS disorder; and (b) obtaining a lipid profile of a sample from the subject, wherein the lipid profile in the sample indicates whether the subject has the CNS disorder.

The invention further provides a method of determining if a mammalian subject has a CNS disorder, the method comprising obtaining a lipid profile of a sample from the subject, wherein the lipid profile from the subject as compared with a standard lipid profile in a mammalian subject without the CNS disorder indicates that the subject has the CNS disorder. According to this embodiment, the standard lipid profile can come from any suitable control subject or population of subjects as would be known to those skilled in the art.

Samples, subjects and lipid profiles are as discussed herein. The diagnostic methods of the invention can be practiced with any combination of features disclosed herein. For example, the lipid profile can evaluate any combination of lipid class, fatty acid chain length, fatty acid saturation/desaturation, and/or position of any double-bonds.

In particular embodiments, the lipid profile evaluates lipid metabolites in two or more lipid classes (e.g., in three or more, four or more, five or more, six or more, seven or more, eight or more classes, etc).

In some methods of the invention, the lipid profile evaluates two or more lipids within one or more lipid classes. Thus, the invention can be practiced to evaluate multiple lipid metabolites, which can be present in the same class, and optionally belong to different subclasses (e.g., different fatty acid moieties), or can belong to two or more lipid classes (e.g., three or more, four or more, five or more, six or more, seven or more, eight or more lipid classes etc).

As discussed above, the methods can be partially or completely quantitative and measure the amount (e.g., a quantitative amount such as weight or moles) of one or more (e.g., optionally all) of the lipid metabolites in the profile. In other embodiments, the methods can be partially or completely relative and, for example, comprise determining the weight % or mole % within class of one or more (optionally all) of the lipid metabolites in the profile.

According to some aspects of the invention, ratios between two or more lipid metabolites (within the same and/or different classes) are determined.

The inventors have discovered that phospholipid metabolism can be perturbed in CNS disorders (e.g., schizophrenia). In some embodiments, the invention comprises detecting a phospholipid metabolite in the sample, wherein a change (e.g., increase or decrease) in the level of the phospholipid metabolite (e.g., quantitative or relative) indicates that the subject has the CNS disorder. The phospholipid(s) can comprise a phosphatidylethanolamine metabolite and/or a phosphatidylcholine metabolite, which can further optionally comprise a polyunsaturated fatty acid moiety (e.g., a long chain polyunsaturated fatty acid moiety).

According to particular diagnostic methods of the invention, a phospholipid metabolite (e.g., a phosphatidylcholine metabolite and/or a phosphatidylethanolamine metabolite) comprising an n3, n6 and/or n9 fatty acid moiety is evaluated, wherein a reduction in the phospholipid metabolite comprising an n3, n6 and/or n9 fatty acid moiety indicates that the subject has the CNS disorder.

In other embodiments, one or more ratios of metabolites in a lipid biosynthetic and/or degradation pathway are determined to evaluate enzyme activities. For example, enzymes involved in elongation (e.g., elongase) and/or saturation and/or desaturation of fatty acids (e.g., delta 5 and/or delta 6 desaturase) can be evaluated (see, e.g., the pathways shown in FIG. 5A and FIG. 5B). Such analysis can point to modulation (increase or decrease) in enzyme activity(ies) associated with disease, response to therapy and/or side effects from therapy. For example, one or more ratios of precursors/products in the pathway of FIG. 5A and FIG. 5B can be evaluated to determine perturbations in the pathway associated with disease and/or side effects to therapy and/or to determine normalization following therapy.

Methods of evaluating enzyme activities in fatty acid biosynthetic pathways based on ratios of various lipid precursors and products, and detecting perturbations in such pathways in disease states are known in the art (see, e.g., Attie et al., (2002) *J. Lipid Res.* 43:1899-1907 and Pan et al., (1995) *J. Clin. Invest* 96:2802-2808).

In practicing this aspect of the present invention, ratios can be evaluated within class. Alternatively, ratios of fatty acids can be evaluated across classes. Ratios can be based on quantitative or relative (e.g., mole percent) measurements.

In some embodiments of the invention, the CNS disorder is schizophrenia. Thus, in practicing the methods of the invention, the amount (i.e., a quantitative amount such as weight or moles) of one or more of the lipid metabolites in Table I (e.g., two or more, three or more, four or more, five or more, six or more, seven or more, ten or more, and the like) can be determined. In representative embodiments, a change in the amount of the one or more lipid metabolites as shown in Table I (i.e., increase or decrease) indicates that the subject has schizophrenia. As discussed above, when multiple lipid metabolites are evaluated, they can belong to the same class (optionally different subclasses) and/or can be members of different classes.

In some embodiments, diagnostic methods for schizophrenia comprise detecting a relative amount (e.g., the weight % or mole % within class) of one or more of the lipid metabolites in Table II (e.g., two or more, three or more, four or more, five or more, six or more, seven or more, ten or more, and the like). In representative embodiments, a change in the relative amount (e.g., weight % or mole % within class) of the one or more lipid metabolites as shown in Table II (i.e., increase or decrease) indicates that the subject has schizophrenia. When multiple lipids are evaluated, they can belong to the same class (optionally different subclasses) and/or can be members of different classes.

Further, as also addressed above, in some embodiments of diagnosing schizophrenia, ratios between two or more lipids (within the same and/or different classes) are determined.

As also discussed above, in some methods of diagnosing schizophrenia according to the invention, the lipid profile evaluates one or more phospholipid metabolites.

According to particular diagnostic methods of the invention, a phospholipid metabolite (e.g., a phosphatidylcholine metabolite and/or a phosphatidylethanolamine metabolite) comprising an n3, n6 and/or n9 fatty acid moiety is evaluated, wherein a reduction in the phospholipid metabolite comprising an n3, n6 and/or n9 fatty acid moiety indicates that the subject has schizophrenia.

Alternatively, or additionally, the method can comprise detecting a phosphatidylethanolamine metabolite comprising a 16:0, 18:0 and/or 18:1 fatty aldehyde moiety, wherein a reduction in the phosphatidylethanolamine metabolite comprising a 16:0, 18:0 and/or 18:1 fatty aldehyde moiety indicates that the subject has schizophrenia.

As discussed above, ratios of reactants/products in a lipid biosynthetic or degradation pathway can shed light on deregulated steps in the pathway associated with schizophrenia and/or side effects from therapy and/or normalization following therapy. For example, in some embodiments, the method can comprise detecting the ratio of 18:0/16:0 in one or more lipid classes (e.g., in the triglyceride class, free fatty acid class, phosphatidylethanolamine class, phosphatidylcholine class and/or lysophosphatidylcholine class), wherein a reduction in the ratio(s) indicates that the subject has schizophrenia. Alternatively or additionally, the method can comprise detecting the ratio of 20:4(n-6)/20:3(n-6) in one or more lipid classes (e.g., in the triglyceride class, free fatty acid class, phosphatidylethanolamine class, phosphatidylcholine class and/or lysophosphatidylcholine class), wherein an increase in the ratio indicates that the subject has schizophrenia.

In practicing this aspect of the present invention, ratios can be evaluated within class. Alternatively, ratios of fatty acids can be evaluated across classes. Ratios can be based on quantitative or relative (e.g., mole percent) measurements.

The invention also provides methods of monitoring the progression of a CNS disorder in a mammalian subject, i.e., using the lipid profile of the subject as a biomarker for the clinical progression of the subject. This aspect of the invention can provide an early predictor of worsening clinical condition and thereby facilitate early therapeutic intervention or alterations in treatment regimen.

Thus, in some aspects, the invention provides a method of correlating a lipid profile with the progression of a CNS disorder in a mammalian subject, the method comprising: (a) obtaining a lipid profile of a sample from a subject with the CNS disorder; and (b) correlating a change in the lipid profile over time with the progression of the CNS disorder.

The invention also provides a method of monitoring the progression of a CNS disorder in a mammalian subject, the method comprising: (a) correlating a lipid profile with the progression of the CNS disorder; (b) obtaining a lipid profile of a sample from the subject; and (c) monitoring changes in the lipid profile in the subject over time, thereby monitoring the progression of the CNS disorder.

Further, in particular embodiments, the method comprises: (a) obtaining a lipid profile of a sample from the subject, wherein the lipid profile is correlated with the progression of the CNS disorder; and (b) and monitoring changes in the lipid profile in the subject over time, thereby monitoring the progression of the CNS disorder.

By monitoring the "progression" of the disorder over time, it is meant that changes in the severity (e.g., worsening or improvement) of the disorder or particular aspects of the disorder are monitored over time.

Samples, subjects, lipid profiles (e.g., lipid signatures for schizophrenia) are as discussed generally hereinabove and with respect to diagnostic methods.

The invention further encompasses prognostic methods, for example, methods of identifying subjects that are at risk of developing a CNS disorder and/or methods of predicting the course of a disease in a subject (e.g., severity and/or rate of progression). The latter aspect can be practiced with a subject that has already been diagnosed with the CNS disorder or is predicted to develop the CNS disorder. Such methods can facilitate prophylactic treatment prior to onset of the disorder and/or choice of an appropriate therapy (for example, an aggressive treatment regimen for a subject that is predicted to develop a severe or rapidly deteriorating form of the disease). Further, prognostic methods can be used when it is desired to classify or separate patients into distinct and different subpopulations, e.g., for the purpose of conducting a clinical trial.

This aspect of the invention can be practiced as a method of correlating a lipid profile with the risk of developing a CNS disorder in a mammalian subject, the method comprising: (a) obtaining a lipid profile of a sample from a subject with the CNS disorder at risk for the CNS disorder; and (b) correlating the lipid profile with the risk of developing the CNS disorder.

The invention also provides a method of determining if a mammalian subject is at risk for a CNS disorder, the method comprising: (a) correlating a lipid profile with the risk of developing the CNS disorder; and (b) obtaining a lipid profile of a sample from the subject, wherein the lipid profile in the sample indicates whether the subject is at risk for the CNS disorder.

Other methods of the invention for determining if a mammalian subject is at risk for a CNS disorder comprise obtaining a lipid profile of a sample from the subject, wherein the lipid profile in the sample as compared with a standard lipid profile in a mammalian subject without the CNS disorder indicates that the subject is at risk for the CNS disorder.

According to this embodiment, the standard lipid profile can come from any suitable control subject or population of subjects as would be known to those skilled in the art.

In other embodiments, the invention provides a method of correlating a lipid profile with a prognosis for the course of a CNS disorder in a mammalian subject, the method comprising: (a) obtaining a lipid profile of a sample from a subject with the CNS disorder; and (b) correlating the lipid profile in the sample with the prognosis for the course of the CNS disorder in the subject.

As another aspect, the invention provides a method of determining a prognosis for the course of a CNS disorder in a mammalian subject, the method comprising: (a) correlating a lipid profile with the course of the CNS disorder; and (b) obtaining a lipid profile of a sample from the subject, wherein the lipid profile in the sample indicates the prognosis for the course of the CNS disorder in the subject.

The invention further provides a method of determining a prognosis for the course of a CNS disorder in a mammalian subject, the method comprising: (a) obtaining a lipid profile of a sample from the subject, wherein the lipid profile is correlated with the prognosis for the course of the CNS disorder; and (b) determining the prognosis for the course of the CNS disorder in the subject.

Samples, subjects and lipid profiles are as discussed herein. The prognostic methods of the invention can be practiced with any combination of features disclosed herein. For example, the lipid profile can evaluate any combination of lipid class, fatty acid chain length, fatty acid saturation/desaturation, and/or position of any double-bonds.

In particular embodiments, the lipid profile evaluates lipid metabolites in two or more lipid classes (e.g., in three or more, four or more, five or more, six or more, seven or more, eight or more classes etc).

According to the prognostic methods of the invention, the lipid profile evaluates one or more lipid metabolites within one or more lipid classes. Thus, the invention can be practiced to evaluate multiple lipid metabolite, which can be present in the same class, and optionally belong to different subclasses (e.g., different fatty acid moieties), or can belong to two or more lipid classes (e.g., in three or more, four or more, five or more, six or more, seven or more, eight or more classes etc).

As discussed above, the methods can be partially or completely quantitative and measure the amount (e.g., a quantitative amount such as weight or moles) of one or more (e.g., optionally all) of the lipid metabolites in the profile. In other embodiments, the methods can be partially or completely relative and comprise determining the relative amount (e.g., weight % or mole % within class) of one or more (optionally all) of the lipids in the profile.

According to some aspects of the invention, ratios between two or more lipids (within the same and/or different classes) are determined.

Thus, in some embodiments, the invention comprises detecting a phospholipid metabolite in the sample, wherein a change (e.g., increase or decrease) in the level of the phospholipid metabolite (quantitative or relative) indicates that the subject has or is at risk for the CNS disorder.

The phospholipid(s) can comprise a phosphatidylethanolamine metabolite and/or a phosphatidylcholine metabolite, which can further optionally comprise a polyunsaturated fatty acid moiety (e.g., a long chain polyunsaturated fatty acid moiety).

According to particular prognostic methods of the invention, a phospholipid metabolite (e.g., a phosphatidylcholine metabolite and/or a phosphatidylethanolamine metabolite) comprising an n3, n6 and/or n9 fatty acid moiety is evaluated, wherein a reduction in the phospholipid metabolite comprising an n3, n6 and/or n9 fatty acid moiety indicates that the subject is at risk for developing schizophrenia and/or provides information regarding the course of the disease.

In other embodiments, one or more ratios of metabolites in a lipid biosynthetic and/or degradation pathway are determined to evaluate enzyme activities. For example, enzymes involved in elongation (e.g., elongase) and/or saturation and/or desaturation of fatty acids (e.g., delta 5 and/or delta 6 desaturase) can be evaluated (see, e.g., the pathways shown in FIG. 5A and FIG. 5B). Such analysis can point to modulation (increase or decrease) in enzyme activity(ies) associated with disease, response to therapy and/or side effects from therapy. For example, one or more ratios of precursors/products in the pathway of FIG. 5A and FIG. 5B can be evaluated to determine perturbations in the pathway associated with risk for developing the disease and/or the course of the disease.

Methods of evaluating enzyme activities in fatty acid biosynthetic pathways based on ratios of various lipid precursors and products, and detecting perturbations in such pathways in disease states are known in the art (see, e.g., Attie et al., (2002) *J. Lipid Res.* 43:1899-1907 and Pan et al., (1995) *J. Clin. Invest.* 96:2802-2808).

In practicing this aspect of the present invention, ratios can be evaluated within class. Alternatively, ratios of fatty acids can be evaluated across classes. Ratios can be based on quantitative or relative (e.g., mole percent) measurements.

In some embodiments of the invention, the CNS disorder is schizophrenia. In representative methods of the invention, the amount (i.e., a quantitative amount such as weight or moles) of one or more of the lipids in Table I (e.g., two or more, three or more, four or more, five or more, six or more, seven or more, ten or more, and the like) can be determined. In some embodiments, a change in the amount (e.g., quantitative) of the one or more lipids as shown in Table I (i.e., increase or decrease) indicates that the subject is at risk for schizophrenia and/or allows for predictions to be made regarding the course of the disease (e.g., severity and/or the rate of progression). As discussed above, when multiple lipids are evaluated, they can belong to the same class (optionally different subclasses) and/or can be members of different classes.

In some embodiments, prognostic methods for schizophrenia comprise detecting the relative amount (e.g., weight % or mole % within class) of one or more of the lipids in Table II (e.g., two or more, three or more, four or more, five or more, six or more, seven or more, ten or more, and the like). In representative embodiments, a change in the relative amount (e.g., weight % or mole % within class) of the one or more lipids as shown in Table II (i.e., increase or decrease) indicates that the subject is at risk for schizophrenia and/or provides information regarding the course of the disease in the subject (e.g., severity and/or rate of progression). When multiple lipid metabolites are evaluated, they can belong to the same class (optionally different subclasses) and/or can be members of different classes.

Further, as addressed above, in some prognostic methods of the invention for schizophrenia, ratios between two or more lipids (within the same and/or different classes) are determined.

As also discussed above, in some prognostic methods according to the invention for evaluating schizophrenia, the lipid profile can evaluate one or more phospholipid metabolites.

According to particular prognostic methods of the invention, a phospholipid metabolite comprising an n3, n6 and/or n9 fatty acid moiety is evaluated, wherein a reduction in the phospholipid metabolite comprising an n3, n6 and/or n9 fatty acid moiety indicates that the subject is at risk for developing schizophrenia and/or provides information regarding the course of the disease. For example, the amount of the reduction may correlate with the severity and/or rate of progression of the disorder.

Alternatively, or additionally, the method can comprise detecting a phosphatidylethanolamine metabolite comprising a 16:0, 18:0 and/or 18:1 fatty aldehyde moiety, wherein a reduction in the phosphatidylethanolamine metabolite comprising a 16:0, 18:0 and/or 18:1 fatty aldehyde moiety indicates that the subject is at risk for developing schizophrenia and/or provides information regarding the course of the disease. For example, the amount of the reduction may correlate with the severity and/or rate of progression of the disorder.

As addressed above, ratios of reactants/products can provide insight into enzyme activities in lipid biosynthetic and/or degradative pathways and highlight perturbations in the pathway associated with risk for developing schizophrenia or the course of the disorder. Thus, in some embodiments, the method can comprise detecting the ratio of 18:0/16:0 in one or more lipid class e.g., in the triglyceride class, free fatty acid class, phosphatidylethanolamine class, phosphatidylcholine class and/or lysophosphatidylcholine class), wherein a reduction in the ratio(s) indicates that the subject is at risk for developing schizophrenia and/or provides information regarding the course of the disease. For example, the amount of the reduction may correlate with the severity and/or rate of progression of the disorder or the risk for developing the disorder.

In practicing this aspect of the present invention, ratios can be evaluated within class. Alternatively, ratios of fatty acids can be evaluated across classes. Ratios can be based on quantitative or relative (e.g., mole percent) measurements.

Pharmacometabolomics.

Pharmacometabolomics is based on the use of the subject's metabolic profile to select appropriate therapeutic (including prophylactic) treatment regimens. This aspect of the invention provides methods of monitoring the efficacy and/or the development of side effects of a particular treatment regimen in a subject (for example, in the context of a clinical trial) already diagnosed with or at risk of developing a CNS disorder. Thus, the invention provides the use of surrogate markers that correlate with treatment efficacy, for example, to determine whether the lipid profile of a subject undergoing treatment partially or completely normalizes during the course of or following therapy or otherwise shows changes associated with responsiveness to the therapy. Further, the invention provides lipid signatures that correlate with the development of adverse side effects associated with a therapy. The lipid signature can be evaluated prior to commencement of therapy (i.e., baseline) or following the commencement of therapy, but generally before the development of the clinical manifestations of the side effects (e.g., within about 2 hours, 4 hours, 6 hours, 12 hours, 1 day, 2 days, 3 days, 4 days, 5 days, 1 week, 2 weeks, 3 weeks, 4 weeks, 6 weeks, 8 weeks, 10 weeks, 12 weeks, 4 months, six months or longer) of commencing therapy. Thus, the invention can be practiced to evaluate the suitability of a therapy early on in the treatment regimen, e.g., prior to the development of side effects. According to this aspect of the invention, the biological sample can be obtained from the subject prior to or after the commencement of therapy, but prior to onset of side effects such as weight gain, hyperlipidemia, metabolic syndrome, and other metabolic perturbations, and is evaluated for changes in the lipid profile that indicate that the patient is at risk for certain side effects and/or is predicted to respond/not respond to the therapy.

Pharmacometabolomics is similar to pharmacogenomics but it is also able to take into account environmental and other non-genetic factors (e.g., other drugs, etc.) that may affect a subject's response to a particular treatment regimen based upon their metaboprint and/or their genotype. Pharmacometabolomics deals with clinically significant hereditary and non-hereditary variations in the response to treatment regimens. In general, several types of pharmacometabolomic conditions can be differentiated. For example, certain pharmacometabolomic conditions can be the result of genetic conditions (e.g., altered drug action or altered drug metabolism). Examples of non-hereditary factors that may affect the efficacy of the treatment regimen and/or the development of adverse side effects include prior or concurrent treatment with other treatment regimens (e.g., drugs), substance dependence/abuse by the subject, the subject's diet, level of exercise, and the like. Thus, pharmacometabolomics permits the selection of effective treatment regimens (prophylactic and/or therapeutic) based on evaluation of the subject's lipid profile. Pharmacometabolomics can further be used to determine appropriate dosages.

As used herein, the term "treatment regimen" refers to prophylactic and/or therapeutic after onset of disease) treatments, unless the context specifically indicates otherwise. The term "treatment regimen" encompasses natural substances and pharmaceutical agents (i.e., "drugs") as well as any other treatment regimen including but not limited to dietary treatments, physical therapy or exercise regimens, electroconvulsive shock therapy, surgical interventions, and combinations thereof. Examples of natural substances for the treatment of CNS disorders include without limitation lipids such as essential fatty acids including choline and omega-3, omega-6 and omega-9 essential fatty acids, which further include but are not limited to arachidonic acid, docasahexaenoic acid, eicosapentaenoic acid, gamma-linolenic acid, dihomo-gamma-linolenic acid, adrenic acid, 22:5n6 fatty acid, 18:4n3 fatty acid, 22:4n3 fatty acid, and/or 22:5n3 fatty acid (see, e.g., U.S. Pat. Nos. 5,198,468 and 5,516,800 to D. F. Horrobin).

Further, the invention can be used to evaluate the effectiveness (i.e., responders/non-responders) or potential adverse side effects of treatment regimens for any other CNS disorder. Exemplary pharmaceutical agents for other CNS disorders include without limitation selective serotonin reuptake inhibitors (SSRIs), tricyclic antidepressants (TCA), serotonin-norepinephrine reuptake inhibitors (SNRI), monoamine oxidase inhibitors (MAOI), benzodiazepine, sedatives, and the like.

The invention can also be used to evaluate the effectiveness (i.e., response or non-response) and/or potential adverse side effects for any treatment regimen for schizophrenia, including typical and/or atypical anti-psychotic agents. Exemplary pharmaceutical agents used to treat schizophrenia include but are not limited to aripiprazole, clozapine, ziprasidone, haloperidol, molindone, loxapine, thioridazine, molindone, thiothixene, pimozide, fluphenazine, luphenazine, resperidone, mesoridazine, quetiapine, trifluoperazine, chlorprothixene, chlorpromazine, perphenazine, trifluopromazine and olanzapine. Other treatment regimens include without limitation natural products such as choline and essential fatty acids including omega-3, omega-6 and omega-9 fatty acids, which further include but are not limited to arachidonic acid, docasahexaenoic acid, eicosapentaenoic acid, gamma-linolenic acid, dihomo-gamma-linolenic acid, adrenic acid, 22:5n6 fatty acid, 18:4n3 fatty acid, 22:4n3 fatty acid, and/or 22:5n3 fatty acid (see, e.g., U.S. Pat. Nos. 5,198,468 and 5,516,800 to D. F. Horrobin).

Thus, the invention provides a method of correlating a lipid profile with an effective treatment regimen for a CNS disorder, the method comprising: (a) obtaining a lipid profile of a sample prior to treatment (i.e., baseline) from a mammalian subject with the CNS disorder; and correlating the lipid profile in the sample with a treatment regimen that is effective for treating the CNS disorder.

The invention further provides a method of determining whether a treatment regimen is effective for treating a mammalian subject with a CNS disorder, the method comprising: (a) correlating a lipid profile prior to treatment (i.e., baseline) with an effective treatment regimen for the CNS disorder; and (b) obtaining a lipid profile of a sample from the subject prior to treatment, wherein the lipid profile in the sample indicates whether the treatment regimen is effective for treating the CNS disorder in the subject.

The invention also encompasses a method of determining whether a treatment regimen is effective for treating a mammalian subject with a CNS disorder, the method comprising: (a) obtaining a lipid profile of a sample from the subject prior to treatment (i.e., baseline), wherein the lipid profile in the sample correlates with an effective treatment regimen for the CNS disorder; and determining whether the treatment regimen is effective for the subject.

CNS disorders, subjects, and lipid profiles are as discussed herein. The pharmacometabolomic methods of the invention can be practiced with any combination of features disclosed herein. For example, the lipid profile can evaluate any combination of lipid class, fatty acid chain length, fatty acid saturation/desaturation, and/or position of any double-bonds.

In particular embodiments, the lipid profile evaluates lipid metabolites in two or more lipid classes (e.g., in three or more, four or more, five or more, six or more, seven or more, eight or more classes etc).

In some methods of the invention, the lipid profile evaluates two or more lipid metabolites within one or more lipid classes. Thus, the invention can be practiced to evaluate multiple lipid metabolites, which can be present in the same class, and optionally belong to different subclasses (e.g., different fatty acid moieties), or can belong to two or more lipid classes (e.g., in three or more, four or more, five or more, six or more, seven or more, eight or more classes etc).

As discussed above, the methods can be partially or completely quantitative and measure the amount (a quantitative amount such as weight or moles) of one or more (e.g., optionally all) of the lipid metabolites in the profile. In other embodiments, the methods can be partially or completely relative and, for example, comprise determining the weight % or mole % within class of one or more (optionally all) of the lipids in the profile.

According to some aspects of the invention, ratios between two or more lipid metabolites (within the same and/or different classes) are determined.

Thus, in some embodiments, the invention comprises detecting a phospholipid metabolite in the sample, wherein a change (e.g., increase and or decrease) as compared with a standard profile in the level of the phospholipid metabolite (quantitative or relative) indicates that the treatment regimen is or is not effective for treating the subject.

The phospholipids metabolite(s) can comprise a phosphatidylethanolamine metabolite and/or a phosphatidylcholine metabolite, which can further optionally comprise a polyunsaturated fatty acid moiety (e.g., a long chain polyunsaturated fatty acid moiety).

In particular embodiments, the CNS disorder is schizophrenia. Treatment regimens for schizophrenia are as described herein.

In particular embodiments, the treatment regimen comprises administration of an atypical anti-psychotic agent including but not limited to resperidone, olanzapine and/or aripipirazole. Optionally, the method comprises detecting the level of DG20:4n6, LY22:5n3, PE20:5n3, PEdm18:1n7 and/or PEdm18:1n9 prior to commencing treatment with an atypical antipsychotic (e.g., resperidone, olanzapine or aripiprazole) to determine whether the atypical antipsychotic agent is an effective treatment for schizophrenia in the subject.

The invention can also be practiced to evaluate whether a subject is responding or not responding (i.e., a negative response) to a treatment regimen and/or to evaluate whether the subject is showing early biochemical changes that indicate the development of adverse side effects to the treatment regimen. This aspect of the invention provides a method of correlating a lipid profile with a positive and/or negative response to a treatment regimen and/or with a side effect for the treatment regimen, the method comprising: (a) obtaining a lipid profile of a sample from a mammalian subject with the CNS disorder following commencement of the treatment regimen; and (b) correlating the lipid profile in the sample with a positive and/or negative response to the treatment regimen and/or with a side effect from the treatment regimen.

The invention also provides a method of determining a positive and/or negative response and/or a side effect to a treatment regimen by a mammalian subject with a CNS disorder, the method comprising: (a) correlating a lipid profile with a positive and/or negative response to the treatment regimen and/or a side effect from the treatment regimen; and (b) detecting the lipid profile of a sample from the subject, wherein the lipid profile in the sample indicates whether the subject is responding to the treatment regimen and/or is developing a side effect from the treatment regimen.

Also encompassed by the invention is a method for determining response and/or side effects to a treatment regimen by a mammalian subject with a CNS disorder, the method comprising: (a) obtaining a lipid profile of a sample from the subject following commencement of the treatment regimen, wherein the lipid profile is correlated with a positive or negative response (i.e., lack of a clinically significant response) to the treatment regimen and/or to a side effect from the treatment regimen; and determining whether the subject is responding to the treatment regimen and/or is developing a side effect from the treatment regimen.

The method can optionally further comprise obtaining the lipid profile of a sample from the subject prior to commencing the treatment regimen (i.e., a baseline profile) and comparing with lipid profile after commencement of the treatment regimen.

This aspect of the invention can be practiced to identify responders/non-responders and/or the development of adverse side effects relatively early in the treatment process, i.e., before clinical manifestations of efficacy and/or side effects. In this way, the treatment regimen can optionally be discontinued, a different treatment protocol can be implemented and/or supplemental therapy can be administered (e.g., to counteract the development of side effects). Thus, in some embodiments, the lipid profile is obtained within about 2 hours, 4 hours, 6 hours, 12 hours, 1 day, 2 days, 3 days, 4 days, 5 days, 1 week, 2 weeks, 3 weeks, 4 weeks, 6 weeks, 8 weeks, 10 weeks, 12 weeks, 4 months, six months or longer of commencing therapy.

For example, the invention facilitates the use of combination therapies for those subjects that are identified as being at a greater risk for the development of certain side effects associated with the treatment regimen. To illustrate, at a relatively early stage those schizophrenia patients undergoing treatment (e.g., with olanzapine) that are at risk for developing obesity, metabolic syndrome and/or type II diabetes mellitus can be identified and given an appropriate therapy to address the perturbations in lipid and carbohydrate metabolism that appear to underlie the increased incidence of metabolic syndrome and/or type II diabetes in these patients.

In some embodiments, the method comprises monitoring the lipid profile over time (i.e., responders/non-responders and/or the development of side effects are evaluated at multiple [two or more] time points).

Changes in the lipid profile following treatment can be determined by comparison with any suitable standard, e.g., untreated or treated normal subjects, untreated affected subjects, subjects undergoing a different therapy, or the same subject prior to the current treatment (i.e., a baseline lipid profile).

CNS disorders, lipid profiles, subjects, and treatment regimens are as discussed herein.

The term "side effect" includes any unwanted reaction or effect in the subject as a result of the treatment regimen and includes without limitation, weight gain, hyperlipidemia, hyperglycemia, insulin resistance, the metabolic syndrome or risk of developing the metabolic syndrome, type II diabetes mellitus or risk of developing type II diabetes mellitus, and other metabolic perturbations, cognitive deficits, extrapyramidal effects, tardive dyskinesia, sleeplessness, lack of libido, and the like.

FIGS. 1-5 and Tables III to V herein map some changes in lipidomic signature in schizophrenic patients following treatment with several atypical antipsychotic drugs. These results point to a systemic defect in triglyceride storage and/or free fatty acid mobilization following certain drug therapies (e.g., olanzapine), and suggest that biochemical pathways associated with triglyceride storage (e.g., lipoprotein lipases, phospholipases including phospholipase c), free fatty acid mobilization and/or triglyceride-free fatty acid cycling, in particular in peripheral tissues (for example, in the liver, adipose tissue, skeletal muscle, pancreas and/or lung), are perturbed by some drug regimens and may be associated with the high incidence of metabolic syndrome and diabetes mellitus observed in schizophrenic patients undergoing some drug therapies (e.g., with olanzapine). These side effects are commonly found in response to treatment of other CNS disorders, and the lipid signatures identified with respect to the administration of atypical antipsychotic agents to schizophrenics are likely relevant to these same side effects for at least some subjects with other disorders/therapies. Although the disorders are different, the underlying biochemical pathways producing the side effects are the same for at least some populations.

In particular embodiments, the lipid profile evaluates lipid metabolites in two or more lipid classes (e.g., in three or more, four or more, five or more, six or more, seven or more, eight or more classes etc).

In some methods of the invention, the lipid profile evaluates two or more lipid metabolites within one or more lipid classes. Thus, the invention can be practiced to evaluate multiple lipid metabolites, which can be present in the same class, and optionally belong to different subclasses (e.g., different fatty acid moieties), or can belong to two or more lipid classes (e.g., in three or more, four or more, five or more, six or more, seven or more, eight or more classes etc).

As discussed above, the methods can be partially or completely quantitative and measure the amount (a quantitative amount in weight or moles) of one or more (e.g., optionally all) of the lipids in the profile. In other embodiments, the methods can be partially or completely relative and, for example, comprise determining the weight % or mole % within class of one or more (optionally all) of the lipid metabolites in the profile.

According to some aspects of the invention, ratios between two or more lipid metabolites (within the same and/or different classes) are determined.

Thus, in some embodiments, the invention comprises detecting a phospholipid metabolites in the sample, wherein the level of the phospholipid metabolite (quantitative or relative) indicates that the subject is having a positive or negative response (i.e., no clinically significant response) to the treatment regimen and/or is/is not developing adverse side effects from the treatment regimen.

The phospholipid metabolite(s) can comprise a phosphatidylethanolamine metabolite and/or a phosphatidylcholine metabolite, which can further optionally comprise a polyunsaturated fatty acid moiety (e.g., a long chain polyunsaturated fatty acid moiety).

Further, the method can comprise detecting a phospholipid metabolite comprising an n3, n6 and/or n9 fatty acid moiety, wherein an increase in the phospholipid metabolite comprising an n3, n6 and/or n9 fatty acid moiety after the commencement of the treatment regimen indicates that the subject is responding positively to the treatment regimen.

A positive response to a treatment regimen can also be evaluated by looking for reversal or normalization of the lipid profiles associated with the CNS disorder (e.g., as discussed above). By "reversal" or "normalization" it is meant a partial or complete normalization.

As a further alternative, one or more ratios of metabolites in a lipid biosynthetic and/or degradation pathway are determined to evaluate enzyme activities. For example, enzymes involved in elongation (e.g., elongase) and/or saturation and/or desaturation of fatty acids (e.g., delta 5 and/or delta 6 desaturase) can be evaluated (see, e.g., the pathways shown in FIG. 5A and FIG. 5B). Such analysis can point to modulation (increase or decrease) in enzyme activity(ies) associated with disease, response to therapy and/or side effects from therapy. For example, one or more ratios of precursors/products in the pathway of FIG. 5A and FIG. 5B can be evaluated to determine perturbations in the pathway associated with disease and/or side effects to therapy and/or to determine amelioration in these perturbations following therapy.

In practicing this aspect of the present invention, ratios can be evaluated within class. Alternatively, ratios of fatty acids can be evaluated across classes. Ratios can be based on quantitative or relative (e.g., mole percent) measurements.

In representative embodiments, the CNS disorder is schizophrenia. The invention can be practiced to evaluate response to a treatment regimen and/or development of side effects in schizophrenic patients being administered any treatment regimen (discussed in more detail hereinabove). In particular embodiments, the treatment regimen comprises administration of a typical or atypical antipsychotic drug.

In embodiments of the invention, the method comprises detecting the ratio of 18:0/16:0; 18:3(n-6)/18:2(n-6); 20:4(n-3)/18:4(n-3) and/or 22:4(n-6)/20:4(n-6) in one or more lipid classes (e.g., in the triglyceride class, free fatty acid class, phosphatidylethanolamine class, phosphatidylcholine class and/or lysophosphatidylcholine class), wherein an increase in the ratio(s) after the commencement of the treatment regimen indicates that the subject is having a positive response to the treatment regimen and, conversely, a decrease in the ratio(s) indicates that the subject is having a negative response (i.e., no clinically significant response) to the treatment regimen.

In other representative embodiments, the method comprises detecting the ratio of 18:1(n-9)/18:0(n-9), 20:4(n-6)/ 20:3(n-6), 20:5(n-3)/20:4(n-3), 22:5(n-3)/20:5(n-3), 22:6(n-3)/22:5(n-3), and/or 24:0/22:0 in one or more lipid classes (e.g., in the triglyceride class, free fatty acid class, phosphatidylethanolamine class, phosphatidylcholine class and/or lysophosphatidylcholine class), wherein a reduction in the ratio(s) after the commencement of the treatment regimen indicates that the subject is responding positively to the treatment regimen.

In practicing this aspect of the present invention, ratios can be evaluated within class. Alternatively, ratios of fatty acids can be evaluated across classes. Ratios can be based on quantitative or relative (e.g., mole percent) measurements.

In other embodiments, a positive response to treatment is indicated by an increase in a phosphatidylcholine metabolite (e.g., total PC) and/or a phosphatidyl ethanolamine metabolite (e.g., PE22:5n6, PEPUFA, PELC and/or PEn6).

A positive response to a treatment regimen can also be evaluated by looking for reversal or normalization of the lipid profiles associated with schizophrenia (e.g., as discussed above and in the Examples). For example, as one aspect, the method can comprise detecting an amount (e.g., a quantitative amount such as moles or weight) of a lipid metabolite in Table I, wherein a reversal or normalization of the change in the amount of the lipid metabolite as shown in Table I (i.e., increase or decrease) after the commencement of a treatment regimen for schizophrenia indicates that the subject is responding positively to the treatment regimen.

Likewise, the method can comprise detecting a relative amount (e.g., mole % within class) of a lipid metabolite in Table II, wherein a reversal or normalization of the change in the mole % within class of the lipid metabolite as shown in Table II after the commencement of a treatment regimen for schizophrenia indicates that the subject is responding positively to the treatment regimen.

Further, the method can comprise detecting a phospholipid metabolite comprising an n3, n6 and/or n9 fatty acid moiety, wherein an increase in the phospholipid metabolite comprising an n3, n6 and/or n9 fatty acid moiety after the commencement of a treatment regimen for schizophrenia indicates that the subject is responding positively to the treatment regimen.

As another aspect, the method can comprise detecting a phosphatidylethanolamine metabolite comprising a 16:0, 18:0 and/or 18:1 fatty aldehyde moiety, wherein an increase in the phosphatidylethanolamine metabolite comprising a 16:0, 18:0 and/or 18:1 fatty aldehyde moiety after the commencement of a treatment regimen for schizophrenia indicates that the subject is responding positively to the treatment regimen.

In particular embodiments, a treatment regimen for schizophrenia comprises administration of resperidone, and optionally further comprises detecting the level of one or more of the lipid metabolites in Table III, wherein a change in the level of the one or more lipid metabolites as shown in Table III indicates that the subject is responding positively to the treatment regimen and/or is developing a side effect to the treatment regimen. In some embodiments of detecting response/nonresponse, one or more phospholipid metabolites (e.g., as shown in Table III) are detected. In some embodiments of detecting side effects, one or more diacylglyceride metabolites, one or more triglyceride metabolites and/or one or more free fatty acid metabolites (e.g., as shown in Table III) are detected. For example, a reduction in total free fatty acids, in n7 free fatty acids and/or n9 free fatty acids can be detected.

In some embodiments, a positive response to resperidone is determined by detecting an increase in a phosphatidylcholine metabolite, a phosphatidylethanolamine metabolite and/or a lysophosphatidylcholine metabolite, optionally metabolites in one or more of these classes comprising a saturated fatty acid moiety. Other changes in lipid metabolites that can indicate a positive response to resperidone include without limitation, an increase in n3 and/or n6 fatty acid moieties across one or more lipid classes (e.g., in the phospholipid classes), and/or an increase in 18:2n6, 18:3n-6, and/or 20:3n-6 fatty acid moieties across one or more lipid classes (e.g., in the phospholipid classes).

In other embodiments, the treatment regimen comprises administration of olanzapine, and optionally further comprises detecting the level of one or more of the lipid metabolites in Table IV, wherein a change in the level of the one or more lipid metabolites as shown in Table IV indicates that the subject is responding positively to the treatment regimen and/or is developing a side effect to the treatment regimen. In some embodiments of detecting response/non-response, one or more phospholipids (e.g., as shown in Table IV) are detected. In some embodiments of detecting side effects, one or more diglyceride metabolites, one or more triglyceride metabolites and/or one or more free fatty acid metabolites (e.g., as shown in Table IV) are detected. For example, an increase in total free fatty acids, in n7 free fatty acids and/or n9 free fatty acids (e.g., 16:1n7, 18:1n7 and/or 18:1n9) can be detected.

In some embodiments, a positive response to resperidone is determined by detecting an increase in a phosphatidylcholine metabolite and/or a phosphatidylethanolamine metabolite, optionally metabolites in one or more of these classes comprising a saturated and/or monounsaturated fatty acid moiety. Other changes in lipid metabolites that can indicate a positive response to resperidone include without limitation, an increase in n3 and/or n6 fatty acid moieties across one or more lipid classes (e.g., in the phospholipid classes), a reduction in the ratio of 20:4n-6/20:3n-6 moieties in the cholesterol ester, phosphatidylethanolamine and/or phosphatidylcholine classes, an increase in the immediate precursors (e.g., 20:5n3 and/or 22:5n3) to docosahexaenoic acid (DHA) across one or more lipid classes (e.g., one or more phospholipids classes) and/or an increase in the immediate precursors to arachidonic acid across one or more lipid classes (e.g., one or more of the phospholipid classes).

In other embodiments, the treatment regimen comprises administration of aripiprazole, and optionally further comprises detecting the level of one or more of the lipid metabolites in Table V, wherein a change in the level of the one or more lipid metabolites as shown in Table V indicates that the subject is responding positively to the treatment regimen and/or is developing a side effect to the treatment regimen. In some embodiments of detecting response/non-response, one or more phospholipids metabolites (e.g., as shown in Table V) are detected. In some embodiments of detecting side effects, one or more diglyceride metabolites, one or more triglyceride metabolites and/or one or more free fatty acid metabolites (e.g., as shown in Table V) are detected.

Mapping of Perturbed Pathways.

Figure 5A:
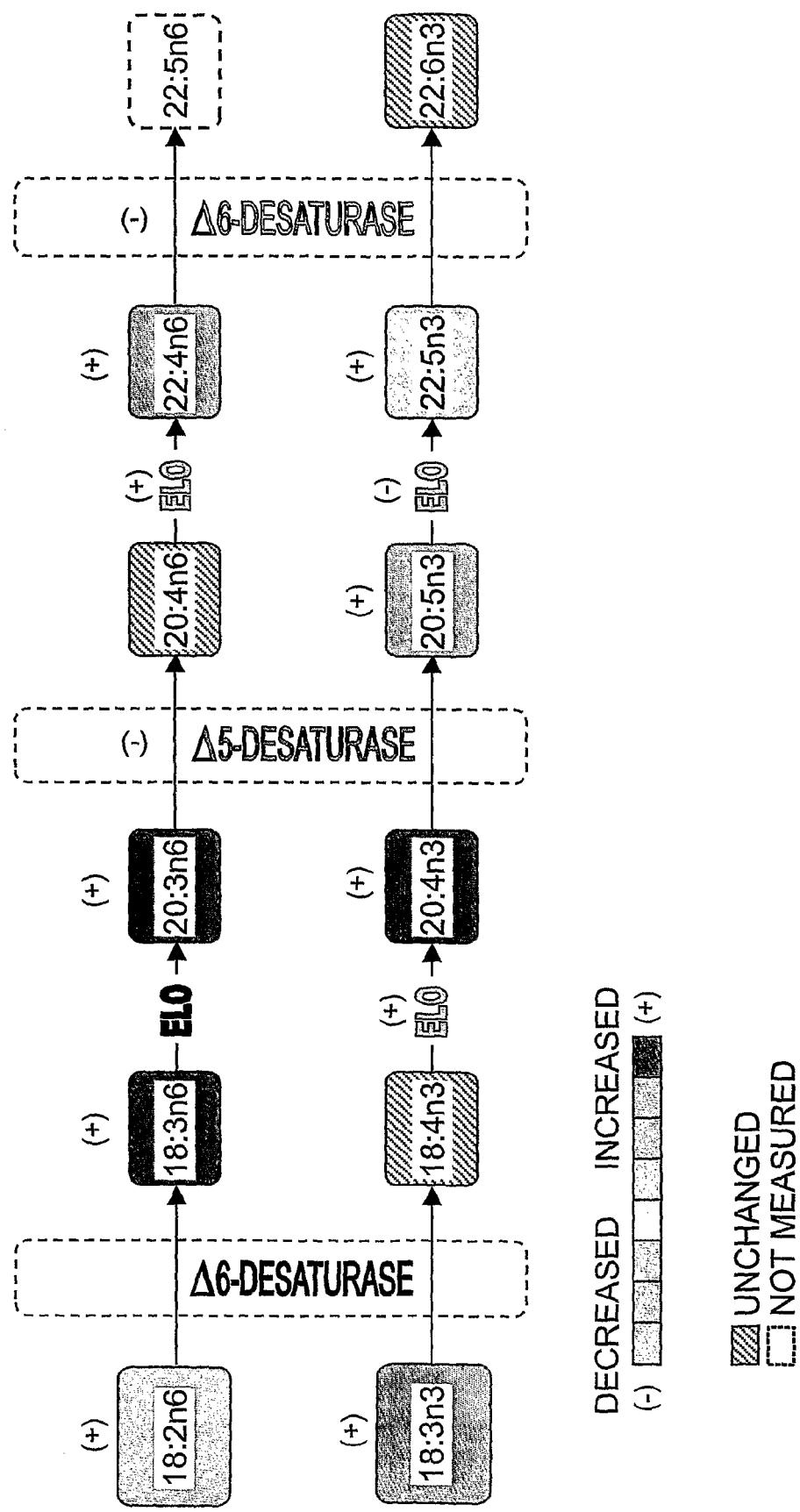
FIGS. 5A and 5B. The regulation of pathways for biosynthesis of phosphatidylcholine n-6 fatty acids in schizophrenic patients post-treatment as compared to pre-treatment with Olanzapine (FIG. 5A) and Risperidone (FIG. 5B). The activities of each of the enzymes were estimated utilizing the ratios of fatty acids (products and reactants) as indicated in the Examples with significant increases (+) and decreases (−) indicated. ELO denotes Elongation.
Figure 5B:
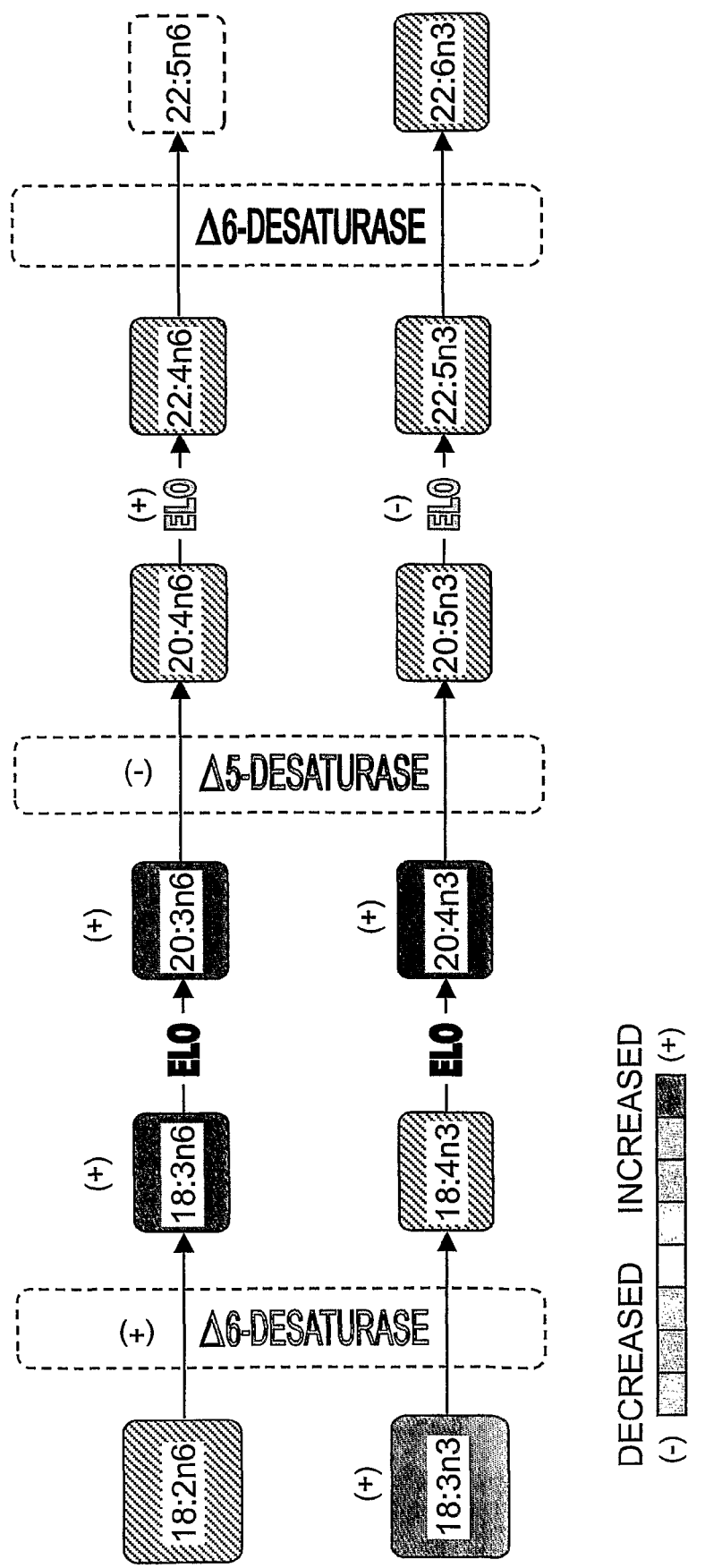

The present invention also enables the mapping of perturbed biochemical pathways, and the constituent binding proteins or enzymes, which provides new targets for drug design, either to treat the CNS disorder and/or to treat the side effects associated with treatment regimens used to treat the CNS disorder (see, e.g., FIG. 5A and FIG. 5B). For example, the finding that triglyceride storage and free fatty acid mobilization are impaired in peripheral tissues (e.g., adipose tissue, liver, skeletal muscle, lung and/or pancreas) in response to some drug therapies for schizophrenia such as olanzapine suggests that these pathways (and the constituent enzymes and binding proteins including lipoprotein lipase, hormone sensitive lipase and phospholipases including phospholipase c) are promising targets for the identification of drugs to treat schizophrenia and/or the metabolic side effects associated with certain drug therapies for this disease. These findings may also be relevant to drug therapies for other CNS disorders, such as depression, which produce some of the same side effects (e.g., weight gain) and may perturb some of the same metabolic pathways.

Thus, compounds that modulate (e.g., activate) biochemical pathways and enzymes that promote triglyceride storage and/or reduce free fatty acid mobilization, in particular, in peripheral tissues, may be advantageous for the treatment of the side effects associated with some anti-schizophrenia (e.g., olanzapine) and anti-depressant (e.g., SSRI) drugs. Conversely, compounds that further enhance the impairment in lipid storage and/or free fatty acid mobilization may have beneficial effects when acting on the brain. Further, compounds that act selectively on the brain without peripheral effects may provide improved therapies with a reduction in adverse side effects.

Biochemical pathways associated with the synthesis or degradation of membrane lipids (including phospholipids), and desaturase enzymes (e.g., to produce arachidonic acid) are also highlighted as drug targets for CNS disorders (including schizophrenia) by the present invention (see, e.g., FIG. 5A and FIG. 5B).

The metabolic signature of drugs and the highlighted biochemical pathways also provide insight into the mechanism of action of particular drugs and facilitate the design of better drugs with decreased side effects and/or improved efficacy.

Databases, User Interfaces, Computer-Readable Media, and Computer Systems.

The invention further provides a computer-readable medium having contained thereon a lipidomic database, wherein the database contains a plurality of records, each record including data (e.g., quantitative or relational) for one or a plurality of metabolites from a biological sample. In particular embodiments, the database is obtained from subjects having a CNS condition or at risk for developing a CNS condition. Further, the database may reflect samples taken prior to and/or after commencement of a treatment regimen. Further, the database can optionally indicate the severity of the subject's condition, the efficacy or lack of efficacy of a treatment regimen, and/or side effects associated with a treatment regimen.

Such databases may be on a computer-readable storage medium, and may be formatted for processing by a computer. Data included in the databases may include any or all of the following:

information that provides for unique identification of data from a sample;

raw measurements of individual lipid metabolites;

transformed measurements of individual metabolites (which have been subject to one or more mathematical transformations from raw data);

basic information about the biological sample (e.g., species, tissue, preparation date, etc.);

genetic information about the subject from which the biological sample was taken (e.g., genotype of a knockout or otherwise engineered animal);

information about any previous diagnosis with a CNS disorder;

health or care history of the subject from which the sample was taken (e.g., long term care strategies, chronic conditions, etc.);

information about the treatment of the subject from which the biological sample was taken (e.g., drug application, feeding schedule or diet, stressors, environment, or toxins);

information about the harvesting of the individual sample and/or the processing of the sample;

information about the individual lipid metabolites (e.g., biochemical or biological characteristics);

information about one or more of the implicated metabolic pathways;

one or more metabolite fingerprints that are associated with a CNS disorder, treatment, genotype, and/or drug application (e.g., to serve as a baseline or control sample);

information linking the treated or test samples to their experimental control samples;

information about the analytical process of producing data; and/or information about the laboratory, investigator and analytical chemists responsible for producing the data.

The provided databases may serve to organize lipid metabolite information, or any of the other information types indicated, in one or more tables. Such tables are readily translatable into database languages such as SQL, and the databases optionally can be integrated with an on-line Internet site containing results of user-defined metabolite analyses.

Another embodiment is a user interface for operatively working with a processor to affect operation of a database as provided herein, where the user interface includes means for providing settings for selecting a set of samples, means for providing settings for selecting a set of conditions, means for providing settings for selecting a set of lipid metabolites, and means for displaying lipidomic profiles corresponding to the selected samples and conditions, wherein each displayed lipidomic profile includes the measurement (e.g., quantitative or relational) of the selected lipid metabolite(s). Optionally, the user interface can further include a display area that displays the measurement of a lipid metabolite within the lipidomic profiles of the selected samples and conditions. Optionally, the user interface can further include means for comparing lipidomic profiles corresponding to a first set of selected samples and conditions to the lipidomic profiles corresponding to a second set of selected samples and conditions, and means for displaying the comparison.

Another embodiment of the invention provides a computer implemented method for operating a relational database which method involves creating a profile table including a lipidomic profile from a biological sample from an individual having a condition, wherein the lipidomic profile comprises a quantified measurement of a lipid metabolite and wherein the quantified measurement is obtained using an internal standard for the lipid metabolite so that the quantified measurement is integratable into a database, creating a sample item table including a sample record for the quantified lipidomic profile, creating a condition item table including a condition record for the quantified lipidomic profile, and storing data in the profile table, the sample item table, and the condition item table, wherein each quantified lipidomic profile corresponds to a sample record and a condition record.

Yet a further embodiment is a computer system for analyzing quantitative lipidomic information, which system includes a processor; and a storage medium storing a relational database accessible by the processor, wherein the storage medium has stored thereon: the relational database comprising: a first table including a plurality of records, wherein at least one of the records includes quantitative data for a plurality of lipid metabolites. Specific examples of such computer systems include a processor, and a storage medium storing a relational database accessible by the processor, wherein the storage medium having stored thereon a relational database comprising a profile table including a quantified lipidomic profile from a biological sample of a condition, wherein the quantified lipidomic profile comprises a quantified measurement of a lipid metabolite and wherein the quantified measurement is obtained using an internal standard for the metabolite so that the quantified measurement is integratable into the relational database, a sample item table including a sample record for the quantified lipidomic profile, and a condition item table including a condition record for the quantified lipidomic profile.

Methods of analyzing/mining the databases of the invention and presentation of the data provided therein (i.e., format of data output) are known in the art, see, e.g., U.S. Patent Publication No. 2004/0143461 A1 (S. M. Watkins).

Having described the present invention, the same will be explained in greater detail in the following examples, which are included herein for illustration purposes only, and which are not intended to be limiting to the invention.

TABLE I compounds significantly different between patients with schizophrenia and controls as determined by quantitative calculations
Quantitative

| Neutral lipid | | Phospholipid | |
|---|---|---|---|
| Metabolites | pvalue | Metabolites | pvalue |
| CE14.1n5 | 0.017353 | LY18.0 | 0.021298 |
| CE18.3n3 | 0.003979 | LY20.4n3 | 0.018083 |
| CE18.3n6 | 0.027233 | PC14.0 | 0.015703 |
| DG22.1n9 | 0.040262 | PC18.0 | 0.004829 |
| FA22.4n6 | 0.002543 | PC18.3n3 | 0.024297 |
| TG18.4n3 | 0.023361 | PC18.3n6 | 0.016972 |
| TG20.4n3 | 0.022243 | PC18.4n3 | 0.021155 |
| | | PC20.3n6 | 0.016955 |
| | | PC20.4n3 | 0.004466 |
| | | PC20.5n3 | 0.00805 |
| | | PCdm16.0 | 0.029257 |
| | | PE16.1n7 | 0.052739 |
| | | PE18.1n9 | 0.02201 |
| | | PE18.2n6 | 0.038229 |
| | | PE20.3n6 | 0.001974 |
| | | PE20.3n9 | 0.008834 |
| | | PE20.4n6 | 0.030375 |
| | | PE22.0 | 0.029752 |
| | | PE22.4n6 | 0.040581 |
| | | PE22.5n3 | 0.001076 |
| | | PEdm | 0.002967 |
| | | PEdm16.0 | 0.001498 |
| | | PEdm18.0 | 0.006569 |
| | | PEdm18.1n7 | 0.02282 |
| | | PEdm18.1n9 | 0.009924 |
| | | PELC | 0.02918 |
| | | PEMUFA | 0.037502 |
| | | PEn6 | 0.020922 |
| | | PEn9 | 0.022022 |
| | | PEPUFA | 0.021706 |
| | | SP14 | 0.0292 |
| | | SP14:1n5 | 0.0123 |
| | | SP20:3n6 | 0.0496 |
| | | SP22 | 0.0233 |
| | | SP24 | 0.0274 |

PE22 is the only metabolite that increased in the baseline, the rest all decreased.

Comparison of lipid metabolites in unmedicated patients with schizophrenia compared with control subjects. Significance of differences using quantitative data (expressed in nmol/g sample) was analyzed by unpaired t-test with p values given. All metabolites were decreased in patients when compared to controls with one exception PE22 which was in creased. Abbreviations: CE, cholesterol ester; CL, cardiolipin; DG, diacylglycerol; FA, free fatty acid; LC, total lipid class; LY, lysophosphatidylcholine; MUFA, mono unsaturated fatty acid; PC, phosphatidylcholine; PE, phosphatidylethanolamine; PUFA, polyunsaturated fatty acid; SFA, saturated fatty acid; SM, sphingomyelin; TG, triacylglycerols.

TABLE II compounds significantly different between patients with schizophrenia and controls as determined by mole percent calculations
Mole percent

| Neutral lipid | | | Phospholipid | | |
|---|---|---|---|---|---|
| Metabolites | pvalue | I/D | Metabolites | pvalue | I/D |
| CE14:1n5 | 0.024927 | D | LY18:0 | 0.000821 | D |
| CE16:0 | 0.042087 | I | LY20:1n9 | 0.039017 | D |
| CE18:1n7 | 0.003769 | I | LY20:4n3 | 0.029065 | D |
| CE18:3n3 | 4.60E−05 | D | PC14:0 | 0.006102 | D |
| CE18:3n6 | 0.050134 | I | PC16:0 | 0.008241 | I |
| FA22:4n6 | 0.047079 | I | PC18:0 | 0.00012 | D |
| TG14:0 | 0.013591 | D | PC18:3n3 | 0.042667 | D |
| TG18:3n3 | 0.042513 | D | PC18:3n6 | 0.045554 | D |
| TG18:4n3 | 0.009988 | D | PC18:4n3 | 0.023465 | D |
| TG20:3n6 | 0.011558 | D | PC20:2n6 | 0.040518 | D |
| TG20:4n3 | 0.001508 | D | PC20:3n6 | 0.022414 | D |
| TG22:5n6 | 0.010186 | I | PC20:4n3 | 0.001845 | D |
| | | | PE.dm | 0.037828 | D |
| | | | PE.SFA | 0.005969 | I |
| | | | PE16:0 | 0.007194 | I |
| | | | PE20:3n6 | 0.04081 | D |
| | | | PE20:3n9 | 0.046872 | D |
| | | | PE22:0 | 0.001535 | I |
| | | | PE22:5n3 | 0.02673 | D |
| | | | PE24:1n9 | 0.041649 | I |
| | | | PEdm16:0 | 0.008644 | D |
| | | | PELC | 0.02918 | D |
| | | | SP14 | 0.0274 | D |
| | | | SP22 | 0.0057 | D |
| | | | SP22:1n9 | 0.0131 | I |
| | | | SP24 | 0.0101 | D |
| | | | SP24:1n9 | 0.0069 | I |
| | | | SPMUFA | 0.0385 | I |
| | | | SPn9 | 0.0179 | I |
| | | | SPSAT | 0.0218 | D |

Comparison of lipid metabolites in unmedicated schizophrenic subjects compared with control subjects. Significance of differences using mole percentage data and total lipid class data (expressed in nmol/g sample) was analyzed by unpaired t-test with p values given. Directionality is post treatment compared with pretreatment. Abbreviations: CE, cholesterol ester; CL, cardiolipin; DG, diacylglycerol; FA, free fatty acid; LC, total lipid class; LY, lysophosphatidylcholine; MUFA, mono unsaturated fatty acid; PC, phosphatidylcholine; PE, phosphatidylethanolamine; PUFA, polyunsaturated fatty acid; SFA, saturated fatty acid; SM, sphingomyelin; TG, triacylglycerols.

TABLE III

Compounds Significantly Modified in Risperidone Treated Patients

| Neutral Lipids | | | Phospholipids | | |
|---|---|---|---|---|---|
| Metabolite | pvalue | I/D | Metabolite | pvalue | I/D |
| CE16:0 | 0.013658 | D | LY.n9 | 0.027279 | I |
| CE18:1n7 | 4.90E−05 | D | LY16:0 | 0.012803 | D |
| CE18:3n3 | 0.000571 | D | LY18:0 | 0.011699 | I |
| CE20:4n6 | 0.001851 | D | LY18:1n7 | 0.02736 | D |
| CE22:6n3 | 0.006301 | D | LY18:1n9 | 0.019228 | I |
| DG18:2n6 | 0.043192 | D | LY18:3n6 | 0.014266 | I |
| DG18:3n6 | 0.022425 | I | LY20:1n9 | 0.029496 | I |
| FA.n6 | 0.011083 | I | LY20:2n6 | 0.041258 | I |
| FA.n9 | 0.002225 | D | LY20:3n9 | 0.008587 | I |
| FA.SFA | 0.001213 | I | LY20:4n3 | 0.031998 | I |
| FA:MUFA | 0.001911 | D | LY20:4n6 | 0.009231 | D |
| FA16:0 | 0.011313 | I | LY22:6n3 | 0.008383 | D |
| FA16:1n7 | 0.030475 | D | LYLC | 0.041236 | I |
| FA18:0 | 0.000274 | I | PC.n9 | 0.018866 | I |
| FA18:1n9 | 0.002272 | D | PC14:0 | 0.003047 | I |
| FA18:2n6 | 0.000757 | I | PC16:0 | 0.023565 | D |
| FA20:4n6 | 0.030031 | I | PC16:1n7 | 0.038906 | I |
| FA20:5n3 | 0.006003 | I | PC18:0 | 0.050568 | I |
| FA24:0 | 0.029495 | I | PC18:1n7 | 0.046225 | D |
| FALC | 0.025628 | I | PC18:1n9 | 0.019281 | I |
| TG14:0 | 0.000529 | I | PC18:3n3 | 0.00035 | I |
| TG14:1n5 | 0.011899 | I | PC18:3n6 | 0.026672 | I |
| TG18:0 | 0.004564 | I | PC20:2n6 | 0.032503 | I |
| TG18:2n6 | 0.030069 | D | PC20:3n9 | 0.017473 | I |

TABLE III-continued

Compounds Significantly Modified in Risperidone Treated Patients

| Neutral Lipids | | | Phospholipids | | |
|---|---|---|---|---|---|
| Metabolite | pvalue | I/D | Metabolite | pvalue | I/D |
| TG18:3n6 | 0.00643 | I | PC20:4n3 | 0.00311 | I |
| TG20:0 | 0.00427 | I | PC20:4n6 | 0.030469 | D |
| TG20:3n6 | 0.040405 | I | PC20:5n3 | 0.044377 | I |
| TG20:4n3 | 0.008416 | I | PC22:6n3 | 0.010865 | D |
| TG20:5n3 | 0.001788 | I | PCLC | 0.021202 | I |
| TG22:5n6 | 0.049036 | D | PE.n7 | 0.039296 | D |
| | | | PE.n9 | 0.049093 | I |
| | | | PE18:1n7 | 0.011607 | D |
| | | | PE18:1n9 | 0.049471 | I |
| | | | PELC | 0.005693 | I |

Comparison of lipid metabolites in subjects before and after treatment with risperidone. Significance of differences using mole percentage data and total lipid class data (expressed in nmol/g sample) was analyzed by paired t-test with p values given. Directionality is post treatment compared with pretreatment. Abbreviations: CE, cholesterol ester; CL, cardiolipin; DG, diacylglycerol; FA, free fatty acid; LC, total lipid class; LY, lysophosphatidylcholine; MUFA, mono unsaturated fatty acid; PC, phosphatidylcholine; PE, phosphatidylethanolamine; PUFA, polyunsaturated fatty acid; SFA, saturated fatty acid; SM, sphingomyelin; TG, triacylglycerols.

TABLE IV

Compounds Significantly Modified in Olanzapine Treated Patients

| Neutral Lipids | | | Phospholipids | | |
|---|---|---|---|---|---|
| Metabolite | pvalue | I/D | Metabolite | pvalue | I/D |
| CE16:0 | 0.015708 | D | LY.n7 | 0.044867 | D |
| CE18:1n7 | 0.001767 | D | LY18:1n7 | 0.003363 | D |
| CE18:3n3 | 0.00174 | I | LY20:3n6 | 0.012679 | I |
| CE18:3n6 | 0.003124 | I | LY20:3n9 | 0.007551 | I |
| CE20:3n6 | 0.000334 | I | LY20:4n3 | 0.001751 | I |
| CE20:4n6 | 0.030369 | D | LY20:4n6 | 0.022908 | D |
| CE20:5n3 | 0.006994 | I | LY20:5n3 | 0.040845 | I |
| CE22:6n3 | 0.038613 | D | LY22:1n9 | 0.046778 | D |
| CE.SFA | 0.0483 | D | LY22:6n3 | 0.008345 | D |
| FA16:1n7 | 0.008943 | D | LYdm16:0 | 0.00694 | D |
| FA18:0 | 0.000864 | I | PC.dm | 0.006797 | D |
| FA20:4n6 | 0.04591 | I | PC.n7 | 0.041126 | D |
| FA22:1n9 | 0.007008 | I | PC.n9 | 0.020077 | I |
| FALC | 0.03552 | D | PC16:0 | 0.00214 | D |
| FA18:2n6 | 0.026132 | D | PC18:0 | 0.000161 | I |
| FAn7 | 0.01573 | D | PC18:1n7 | 0.010062 | D |
| FAPUFA | 0.008238 | D | PC18:1n9 | 0.022937 | I |
| FASAT | 0.005795 | I | PC20:2n6 | 0.000163 | I |
| FCLC | 0.050317 | I | PC20:3n6 | 0.000129 | I |
| TG14:0 | 0.010113 | I | PC20:3n9 | 0.000208 | I |
| TG18:1n7 | 0.005798 | D | PC20:4n3 | 0.000342 | I |
| TG18:2n6 | 0.023531 | D | PC20:4n6 | 0.008059 | D |
| TG20:1n9 | 0.022071 | I | PC20:5n3 | 0.004101 | I |
| TG20:3n6 | 0.029025 | I | PC22:0 | 0.043396 | I |
| TGLC | 0.001156 | I | PC22:1n9 | 0.027047 | D |
| TGn6 | 0.02092 | D | PC22:4n6 | 0.003694 | I |
| TG20.4n3 | 0.02452 | I | PC22:6n3 | 0.016899 | D |
| TGPUFA | 0.022831 | D | PCdm16:0 | 0.005744 | D |
| | | | PCdm18:1n7 | 0.002677 | D |
| | | | PCLC | 0.009598 | I |
| | | | PE14:0 | 0.0159 | D |
| | | | PE14:1n5 | 0.010846 | D |
| | | | PE15:0 | 0.013177 | D |
| | | | PE18:3n6 | 0.020775 | I |
| | | | PE20:3n6 | 6.80E−05 | I |
| | | | PE20:3n9 | 0.001441 | I |
| | | | PE20:4n3 | 0.049023 | D |
| | | | PE20:5n3 | 8.00E−04 | I |
| | | | PE22:5n6 | 0.046313 | I |
| | | | PE22:6n3 | 0.006465 | D |
| | | | PELC | 0.012539 | I |
| | | | SP14:0 | 0.00781 | I |
| | | | SP20:3n6 | 0.01377 | I |
| | | | SP24:1n9 | 7.23E−05 | D |
| | | | SPMUFA | 0.00036 | D |

TABLE IV-continued

Compounds Significantly Modified in Olanzapine Treated Patients

| Neutral Lipids | | | Phospholipids | | |
|---|---|---|---|---|---|
| Metabolite | pvalue | I/D | Metabolite | pvalue | I/D |
| | | | SPn9 | 0.00018 | D |
| | | | SPSAT | 0.00271 | I |

Comparison of lipid metabolites in subjects before and after treatment with olanzapine. Significance of differences using mole percentage data and total lipid class data (expressed in nmol/g sample) was analyzed by paired t-test with p values given. Directionality is post treatment compared with pretreatment. Abbreviations: CE, cholesterol ester; CL, cardiolipin; DG, diacylglycerol; FA, free fatty acid; LC, total lipid class; LY, lysophosphatidylcholine; MUFA, mono unsaturated fatty acid; PC, phosphatidylcholine; PE, phosphatidylethanolamine; PUFA, polyunsaturated fatty acid; SFA, saturated fatty acid; SM, sphingomyelin; TG, triacylglycerols.

TABLE V

Compounds Significantly Modified in Aripiprazole Treated Patients

| Metabolite | pvalue | I/D |
|---|---|---|
| CE18:0 | 0.002358 | I |
| CE22:2n6 | 0.025513 | D |
| LY22.5n3 | 0.041946 | I |
| PC22:5n6 | 0.021185 | I |
| PELC | 0.034905 | I |
| SP14:1n5 | 0.011585 | I |
| SP18:3n3 | 0.015745 | I |
| SPSAT | 0.045049 | I |
| TG18:0 | 0.018283 | I |
| TG22:2n6 | 0.04852 | I |

Comparison of lipid metabolites in subjects before and after treatment with aripiprazole. Significance of differences using mole percentage data and total lipid class data (expressed in nmol/g sample) was analyzed by paired t-test with p values given. Directionality is post treatment compared with pretreatment. Abbreviations: CE, cholesterol ester; CL, cardiolipin; DG, diacylglycerol; FA, free fatty acid; LC, total lipid class; LY, lysophosphatidylcholine; MUFA, mono unsaturated fatty acid; PC, phosphatidylcholine; PE, phosphatidylethanolamine; PUFA, polyunsaturated fatty acid; SFA, saturated fatty acid; SM, sphingomyelin; TG, triacylglycerols.

Example 1

Methods and Materials

Human Subjects.

Fifty male and female patients were recruited in two studies for metabolic profiling (Table VI and Table VII for demographics). Subjects ranged in age from 18 to 60 years and met the following inclusion criteria: a) DSM-IV criteria for schizophrenia, schizophreniform disorder, or schizoaffective disorder; b) newly hospitalized for a psychotic exacerbation in the setting of no antipsychotic treatment for at least 3 weeks prior to admission; and c) provided signed informed consent. Patients with psychoses due to psychoactive substance abuse or an underlying medical condition were excluded. Patients who were receiving treatment for diabetes mellitus or hyperlipidemia were also excluded. The subjects were recruited in two groups and samples were collected pre- and post-treatment with antipsychotics—Study I consisted of 27 patients with schizophrenia (risperidone N=9, olanzapine N=14, aripiprazole N=4); and Study II consisted of 23 new patients with schizophrenia (5 on risperidone, 6 on olanzapine and 12 on aripiprazole).

TABLE VI

Clinical and Demographics for Study I.

| | Aripiprazole | Olanzapine | Risperidone |
|---|---|---|---|
| N | 4 | 14 | 9 |
| Age | 31.3 ± 10.5 | 33.4 ± 3.5 | 30.8 ± 3.8 |
| Height (in) | 68.5 ± 1.2 | 67.8 ± 1.3 | 68.1 ± 1.1 |
| Weight (lbs) | 149 ± 17.3 | 170 ± 8.3 | 176.4 ± 14.1 |
| CGI Positive, Pre | 4.8 ± 0.3 | 5.1 ± 0.1* | 5 ± 0.3 |
| CGI Negative, Pre | 1.8 ± 0.5 | 3 ± 0.3 | 2.2 ± 0.4 |
| CGI Affective, Pre | 3 ± 0.6 | 2.3 ± 0.3 | 2.6 ± 0.5 |
| # Days Treated | 15.8 ± 3.4 | 24.6 ± 2.5* | 18.5 ± 2.8 |
| CGI Positive, Post | 2.5 ± 0.3 | 2.9 ± 0.2 | 2.6 ± 0.2 |
| CGI Negative, Post | 1.3 ± 0.3 | 2.2 ± 0.3* | 2 ± 0.4 |
| CGI Affective, Post | 1.5 ± 0.3 | 1.5 ± 0.2 | 1.7 ± 0.3 |
| CGI Change, Post | 2.5 ± 0.3 | 2.8 ± 0.2 | 2.9 ± 0.3 |
| % AA | 75 | 64.3 | 77.7 |
| % Male | 75 | 85.7 | 88.8 |
| % First Episode | 50 | 21.4 | 44.4 |

Data is presented as means and standard error of patient characteristics.
*Difference between Sets p < 0.05.
Difference between Treatments p < 0.05.

TABLE VII

Clinical and Demographics for Study II.

| | Aripiprazole | Olanzapine | Risperidone |
|---|---|---|---|
| N | 12 | 6 | 5 |
| Age | 30.5 ± 3 | 28 ± 4.5 | 31.2 ± 6.2 |
| Height (in) | 67.9 ± 1.4 | 69.2 ± 2.8 | 71.2 ± 1.2 |
| Weight (lbs) | 162.5 ± 9 | 162.3 ± 16.7 | 198.4 ± 26.2 |
| CGI Positive, Pre | 4.6 ± 0.2 | 4.2 ± 0.2*# | 5.4 ± 0.5# |
| CGI Negative, Pre | 2 ± 0.4 | 2.2 ± 0.5 | 2 ± 0.3 |
| CGI Affective, Pre | 2.1 ± 0.3 | 1.8 ± 0.7 | 2.4 ± 0.5 |
| # Days Treated | 14 ± 1.2 | 14 ± 1.9* | 15 ± 2.6 |
| CGI Positive, Post | 2.5 ± 0.2 | 2.4 ± 0.2 | 3 ± 0.3 |
| CGI Negative, Post | 1.6 ± 0.3 | 1 ± 0* | 1.4 ± 0.2 |
| CGI Affective, Post | 1.4 ± 0.2 | 1.2 ± 0.2 | 1.2 ± 0.2 |
| CGI Change, Post | 2.8 ± 0.2 | 3 ± 0.3 | 3 ± 0.3 |
| % AA | 58.3 | 66.6 | 80 |
| % Male | 75 | 66.6 | 100 |
| % First Episode | 33.3 | 50 | 40 |

Data is presented as means and standard error of patient characteristics.
*Difference between Sets p < 0.05.
Difference between Treatments p < 0.05.

Environment for Patients.

All patients remained hospitalized for the entirety of their participation. The diet available to them from the hospital cafeteria was similar to the standard diet served in homes and restaurants. They also had access to vending machines and meals brought by visitors. Other than being required to attend group activities for 4-6 hours per day, their activity level was not restricted. Smoking was available to them only during 5 brief smoking breaks throughout the day.

Controls.

Sixteen control subjects who matched the patient sample in age, gender, and race were also recruited. Control subjects were excluded if they or any of their first-degree relatives had a major psychiatric disorder, or if they were receiving treatment for diabetes mellitus or hyperlipidemia. All control subjects were nurses or health care technicians at the hospital.

Pharmacologic Treatment.

The choice and dose of antipsychotic medication was based on the doctor's judgment. Risperidone doses ranged between 2-6 mg daily, olanzapine doses ranged between 10-30 mg daily, and aripiprazole doses ranged between 10-15 mg daily. The treatment duration was 2-3 weeks. Average treatment time in Study 1 was 21.9 days and duration was not significantly different between risperidone and olanzapine (19 and 24 days) but was slightly shorter for aripiprazole (16 days) (p=0.10). The mean duration of therapy was about 2 weeks for all 3 drugs in Study II. The drug groups were otherwise generally similar in severity of disease and physical characteristics (Table VI and Table VII). The 2-3 week duration permits the study of acute early effects.

Psychopathology Assessments.

Psychopathology was assessed on the Clinical Global Impressions (CGI) Scale at baseline and at the time of follow-up blood draws. Scores for the CGI Scale can range from 1 to 7, with higher scores indicating greater severity of illness (Guy (1975) *ECDEU Assessment Manual for Psychopharmacology: Publication ADM* 76-338. Washington, D.C.: US Department of Health, Education, and Welfare). An overall global change rating was also made at the time of the follow-up blood draw. The three treatment groups did not differ on the years since first treated, or psychopathology measures at time of enrollment in the study, and all three groups showed similar patterns of treatment response (Table VI and Table VII).

Plasma Sampling.

All blood samples were drawn from subjects in the early morning after overnight fasting. Blood was drawn into vacutainer tubes containing sodium heparin, immediately placed on ice, and within 10 minutes, the blood was centrifuged and the plasma was transferred into polypropylene tubes and stored in a −30° C. freezer. All baseline samples were drawn prior to starting antipsychotic treatment in the study. If a patient had received a dose of an antipsychotic during the referral process (e.g., because of agitation when initially seen in a local emergency department), drawing of baseline plasma samples was delayed for 2-3 days. Follow-up samples were drawn after patients had received an average of 2-3 weeks of acute antipsychotic treatment.

Lipid Profiling.

A comprehensive assessment of plasma lipid profiles was performed (Lipomics Technologies, West Sacramento, Calif.) according to established methods (Watkins, et al. (2002) *J. Lipid Res.* 43(11):1809-17). Quantitative measurements of fatty acids in various lipid classes were determined as nmol fatty acid/gram of plasma. Lipid classes included cholesterol esters (CE), free cholesterol (FC), triacylglycerols (TG), diacylglycerols (DG), free fatty acids (FA), lysophosphatidylcholine (LY), phosphatidylcholine (PC), and phosphatidylethanolamine (PE). Lipid metabolites are identified by the lipid class and the fatty acid moiety. In the context of this invention, fatty acids are identified first by the number of carbons in the molecule (e.g., 20), the number of double bonds in the molecule (e.g., 4), and lastly the position of the double bonds (e.g., n6). To illustrate, PC20:4n6 denotes a phosphatidylcholine molecule containing a 20 carbon fatty acid with 4 double bonds at the n6 position.

Pathway Analyses.

Estimates of lipid synthesis enzyme activities were calculated using the precursor to product ratios for each enzyme. The following ratios were used: 18:3n6/18:2n6 for delta 6 desaturase; 20:3n6/18:3n6 for delta 6 elongase; 20:4n6/20:3n6 for delta 5 desaturase; 22:4n6/20:4n6 for elongase; 24:4n6/22:4n6 for elongase; 24:5n6/24:4n6 for delta 6 desaturase. The absolute numbers for each fatty acid metabolite were used for calculating metabolite changes.

Statistical Analyses.

Significant differences between pre- and post-drug treatment were assessed by paired t-tests. Evaluation of response to drug was assessed by two-way ANOVA. All statistics were done using R with the following functions: t.test, anova, prcomp, and g/m (Team RDC (2005) R: A language and environment for statistical computing. *R Foundation for Statistical Computing*). Before beginning statistical analyses, change detection was used to determine if observed signals were greater than that which could be expected by chance (noise). The chance distribution of p-values was determined by permuting the outcome groupings (Golub, et al. (1999) *Science* 286(5439):531-7). Briefly, P values for the appropriate comparison were calculated for each metabolite using a Student's t-test. The metabolites were ranked by p value from smallest to largest. The log of the rank versus the log of the p value for each comparison of interest was plotted and is represented by a colored line. The distribution of p values expected by chance at each rank is indicated by the shaded area. The chance distribution was determined by a Monte Carlo permutation method applied to a dataset in which the post-treatment and controls had been scaled to the same mean value and combined. Z-scores were calculated from the area under the curve (AUC) of the treatment group compared to the distribution of the AUC for the random permutations. The Z-values patients are indicated as an increase (+), while metabolites significantly lower are indicated as a decrease (−). With the exception of PE class, which was significantly decreased in schizophrenic patients, all other lipid class totals did not differ significantly between the two groups (FIG. 1A). Within the PE class there were decreases in the n3, n6, and n9 fatty acid family moieties and in the fatty aldehyde (16:0, 18:0 and 18:1) moieties of plasmalogen (FIG. 1A). There was a non-significant trend toward a decrease in PC class.

Example 3

Antipsychotic Effects (Study I)

Risperidone Effects.

Figure 1B:
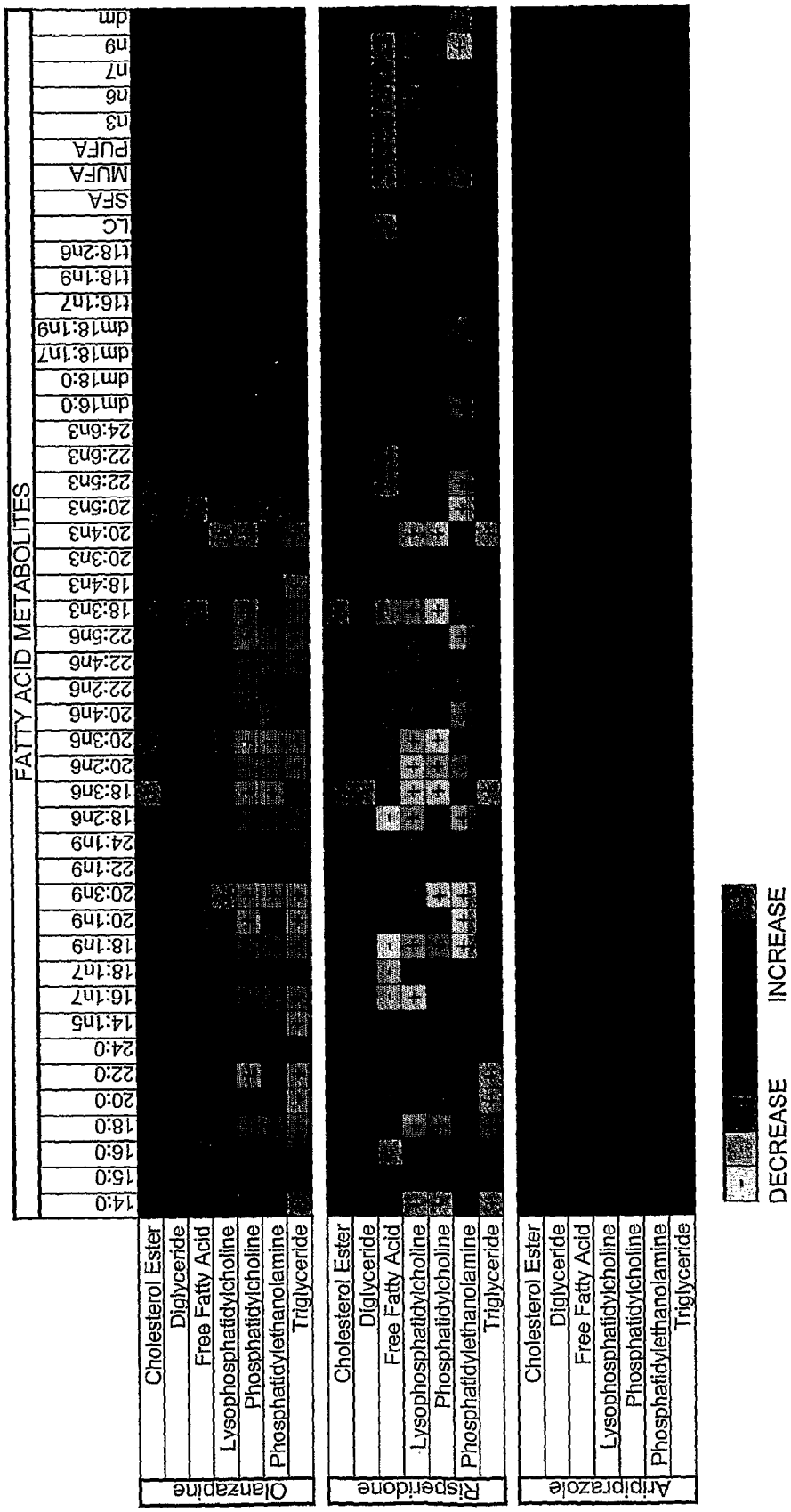

The effect of risperidone on lipids within eight major classes is shown in the heatmap of FIG. 1B. Heatmaps for drug effects described below were created by testing the significance of each treatment (post-treatment vs pre-treatment) on the metabolite concentration using a paired Student's t-test as described in Example 1. If the treatment effect was significant at alpha of 0.05, a mean percentage difference in the concentration of the metabolite induced by treatment was calculated. Metabolites significantly increased by treatment are indicated by squares marked with a "+", while metabolites significantly decreased by are indicated by squares marked with a "-", Risperidone treatment increased concentrations of two phospholipid classes PE and PC, which were reduced pre-treatment in schizophrenic patients (p=0.005, 0.02) (FIG. 1B). There was also an increase in LY class (which is derived from PC). The three phospholipid classes (PE, PC and LY) exhibited similar modifications of fatty acid levels (FIG. 1B). The concentration of saturated fatty acids increased in each of the lipid classes. The concentration of total n6 and n3 fatty acids increased, yet not to the same extent (FIG. 1B). The concentration of linoleic acid (18:2n6), precursor to the dietary-derived omega 6 family, and the immediate metabolic products of this fatty acid 18:3n6 and 20:3n6 were also increased. However, the concentration of arachidonic acid, AA (20:4n6), was not significantly altered in any lipid class with a slight increase in PE. The concentration of linoleic acid (18:2n6) increased in all lipid classes except free fatty acids. Other changes in lipids included a decrease in FA (p=0.02) and a trend toward an increase in DG, TG and CE concentrations with specific fatty acid changes within each lipid class highlighted (FIG. 1B).

Olanzapine Effects.

There were increases in phospholipid classes PE and PC, which were reduced pre-treatment in schizophrenic patients (p=0.01, 0.009), were used to evaluate it there was a treatment effect. For the smallest p value that could be obtained by chance, there were at least five smaller p-values in the olanzapine group and 22 smaller p-values in the risperidone group. The distribution of p-values in the aripiprazole group was similar to the control subjects.

Heat maps were used to visualize differences between schizophrenic patients and healthy controls as well as the differences in the treatment effects in schizophrenic patients. Heat maps were created by testing the significance of each treatment on the metabolite concentration using a paired Student's t-test (for the baseline study that compares controls and patients, unpaired Student's t-test was used). If the treatment effect was significant at alpha of 0.05, a mean percentage difference in the concentration of the metabolite induced by treatment was calculated. The heatmap can be read as follows: the column headers display the fatty acid and the row headers the family of fatty acids present in each lipid class. Each cell in the heatmap represents a standardized observation for a particular metabolite. Metabolites significantly increased by treatment were displayed in red, while metabolites significantly decreased by treatment were displayed in green. The brightness of each color corresponded to the magnitude of the difference in quartiles. The brighter the square is the larger the difference.

Logistic regression was used to identify a set of pretreatment lipid metabolites that were related to drug response. Principal component analysis (PCA) was then used to examine how well a selected group of lipids separates two groups of interest: responders who had a CGI change score of 1-2 and non-responders who had a score of 3-6. Principal component analysis (PCA) is a way to explain the variance-covariance structure of a set of variables through a few linear combinations of those variables. Its general objectives are data reduction, interpretation, and dealing with highly correlated variables. PCA can reveal relationships that were not previously suspected, and allow a novel interpretation of the data.

Example 2

Baseline Analyses

At baseline, and prior to administration of antipsychotic medications, the level of eight lipid classes between 27 schizophrenic patients (Study 1) and 16 healthy controls were compared. These lipid classes were CE, FC, TG, DG, FA, LY, PC, PE. The heatmap (FIG. 1A) shows fatty acids within the eight lipid classes that are significantly different between patients with schizophrenia and controls (see statistics in Example 1). The column headers display the fatty acid and the row headers the family of fatty acids present in each lipid class. Metabolites significantly higher in but no increase in LY class was noted as shown in heatmap FIG. 1B (calculations as above for risperidone). There were increases in CE, FC, and TG concentrations (p=0.056, 0.050, 0.001, respectively) with decreases in FA (p=0.03). As with risperidone, fatty acid changes were specific amongst various lipid classes following olanzapine treatment (FIG. 1B). The concentrations of saturated and monounsaturated fatty acids in TG, PE and PC were increased. The immediate precursors and metabolites of arachidonic acid 20:4n6 were increased, in TG, CE, PE, and PC, but arachidonic acid concentration was only increased in PE after treatment. The ratio of arachidonic acid to its precursor dihomo-linolenic acid (20:4n6/20:3n6) was significantly decreased post-treatment in CE, PE and PC (p=0.0068, 0.0041, 0.0029, respectively). In addition, the immediate precursors of docosahexaenoic acid, DHA (22:6n3) that is 20:5n3 and 22:5n3, were increased following treatment, but not the concentration of docosahexaenoic acid itself.

Aripiprazole Effects.

Minimal significant lipid changes were seen with aripiprazole. Total PE concentrations were increased after treatment with aripiprazole; however, no other total lipid class changes were found and very little change was seen in the fatty acid concentrations (FIG. 1B).

Common Effects.

Figure 1C:
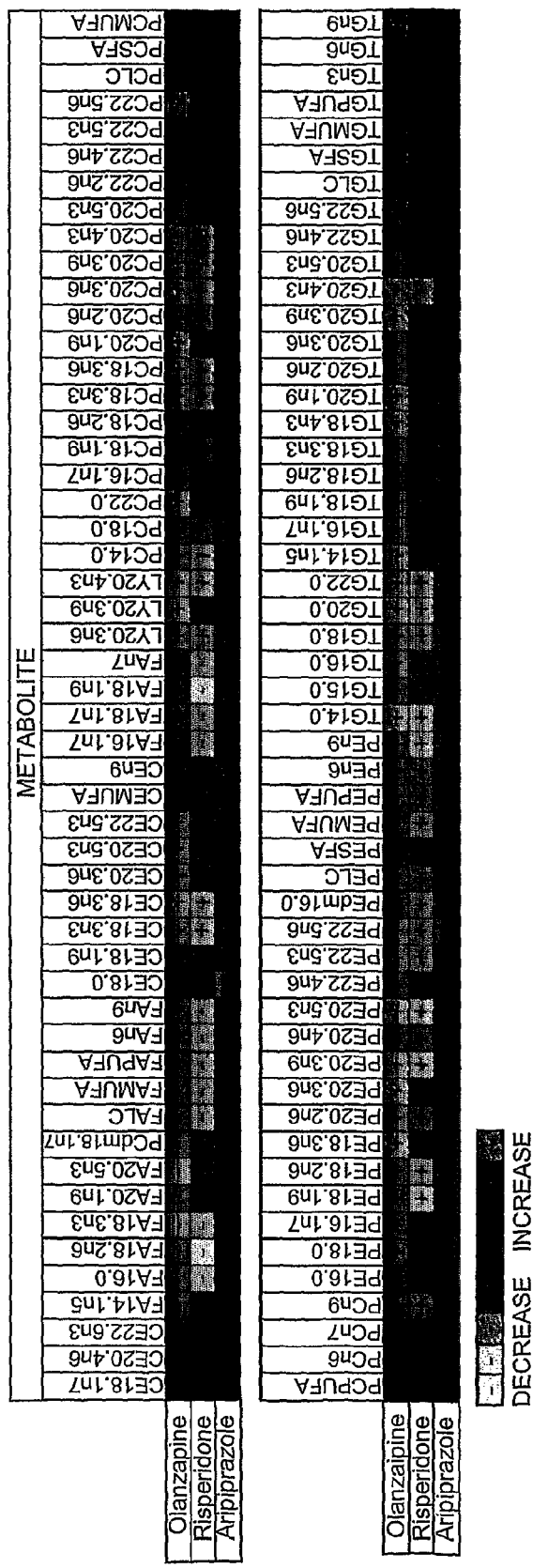

There were only four metabolites that were changed significantly and similarly by all three antipsychotics. These were all PE metabolites including PE22:5n6, the PUFA family in PE, the n6 fatty acid family within PE and total PE, There was a much larger set of lipid metabolites that was significantly and similarly changed by both risperidone and olanzapine (FIG. 1B and FIG. 1C), but there were other effects that were drug-specific. Most notably there were increases in the n7 and n9 free fatty acids in olanzapine patients, decreases in these fatty acids in the risperidone-treated patients, and no change in the aripiprazole-treated patients. FIG. 1C highlights the most significant lipid changes noted with olanzapine and corresponding changes noted with risperidone and aripiprazole in these lipid metabolites.

Change Detection Analysis and Chance Finding Assessment.

Figure 2:
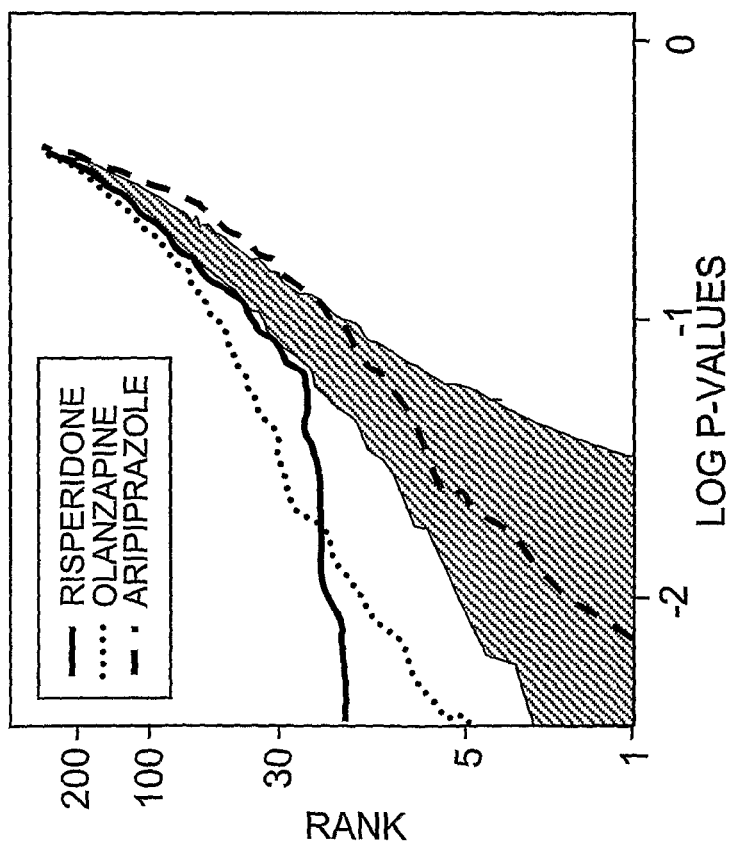
FIG. 2. Change detection plot. Change detection was used to determine if observed signals in lipids from the antipsychotic-treated subjects were greater than that which could be expected by chance. The shaded area represents the number of p-values that would be expected by chance or noise in the data. The p-values for post-treatment of each drug are plotted with aripiprazole as a dashed line, risperidone as a solid line and olanzapine as a dotted line. The rankings of the p-values for both olanzapine and risperidone were above that expected by chance.
Figure 4E:
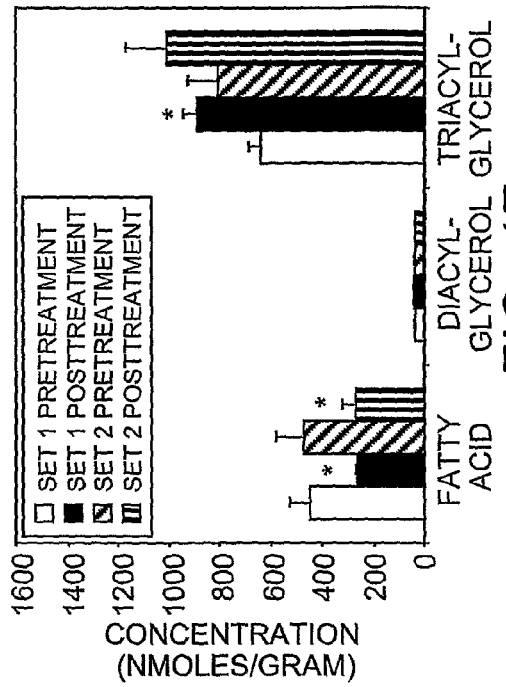
Figure 4F:
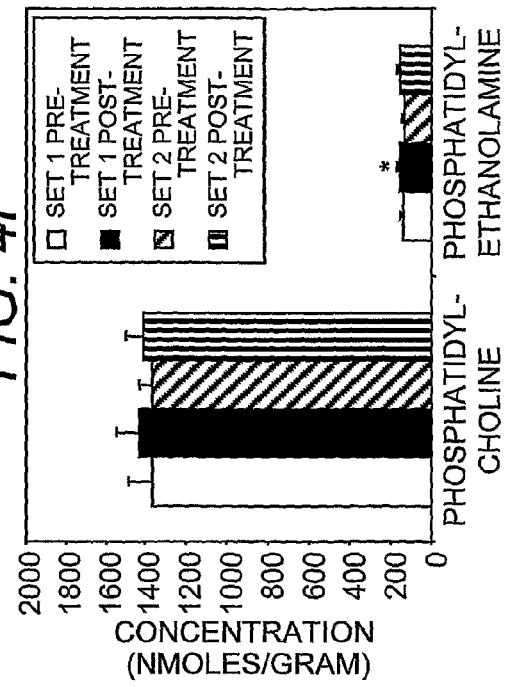
Figure 4G:
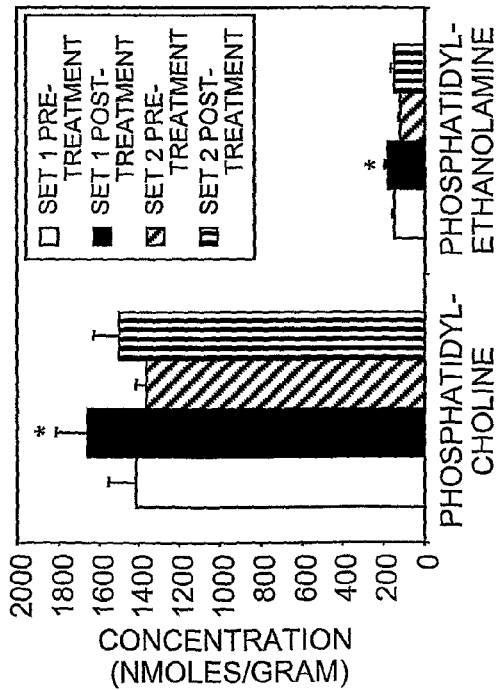
Figure 4H:
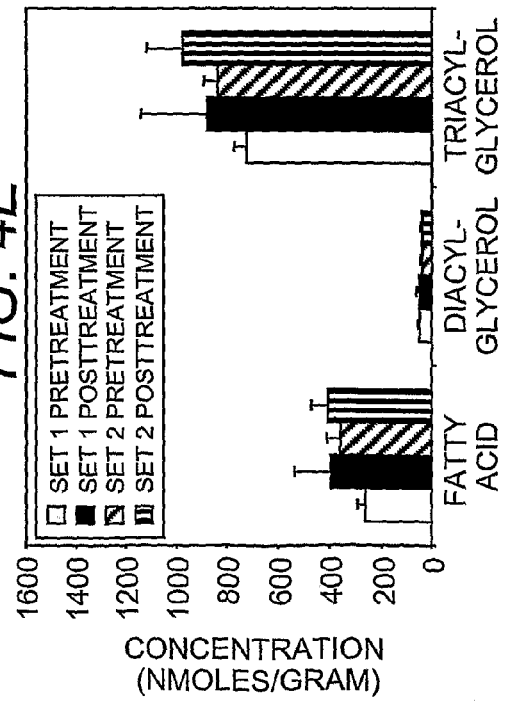

Given that there were a large number of variables were being dealt with and a relatively small number of subjects, the issue of chance and false positives findings were assessed. Change detection (see statistics, Example 1) was used to determine if observed changes in the lipids of the antipsychotic-treated patients were greater than that which could be expected by chance. The rankings of the p-values for drug treatment were then plotted. Both olanzapine and risperidone had more statistically significant p-values than could be expected by chance. For the smallest p-value that could be obtained by chance, there were at least five smaller p-values in the olanzapine group and 22 smaller p-values in the risperidone group (FIG. 2). This indicated that there were true positives in the data for these groups. The distribution of p-values in the aripiprazole group was within the grade shaded area and was not different from that expected by chance.

Biochemical Correlations to Clinical Outcome.

Figure 3:
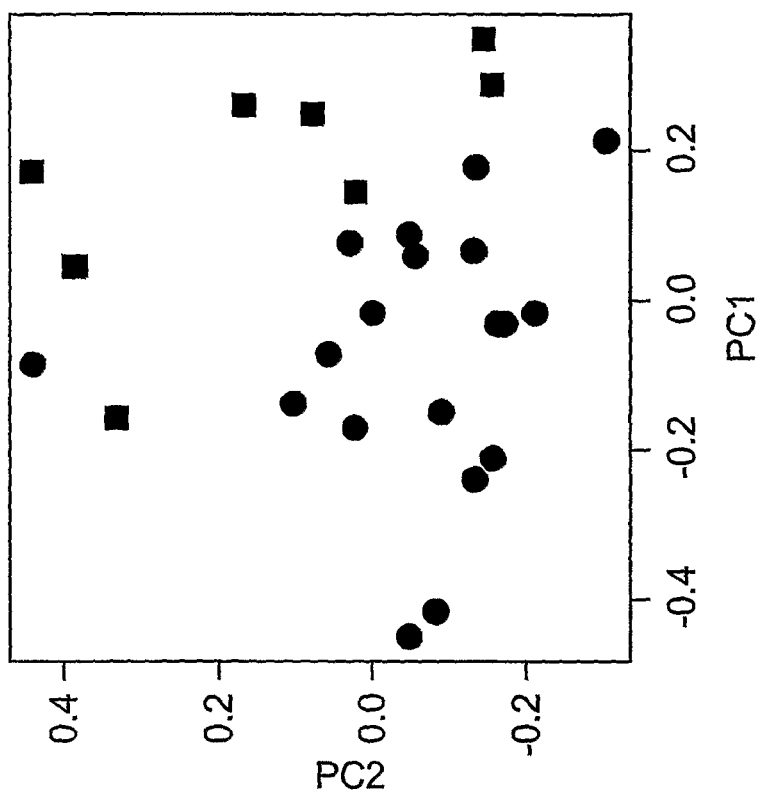
FIG. 3. Principle component analysis for CGI change variable. Logistic regression was used to identify the pre-treatment lipid metabolites that were related to response (responders who had a CGI change score of 1-2 and non-responders who had a score of 3-6). Principle component analysis was then applied to these metabolites and the separation of the groups was visualized by a scatter plot of the first versus the second principal component. Squares are subjects who respond to drug treatment with a CGI change score of 1-2. Circles are subjects who do not respond to drug treatment with a CGI change score of 3-6. Analysis was conducted as described in the Examples.

Baseline DG20.4n6, LY22.5n3, PE20.5n3, PEdm18.1n7, PEdm18.1n9 lipid concentrations were found by logistic regression to correlate with early clinical response in a pooled analysis of all three antipsychotics. Principal component analysis (PCA) was then used to examine how well the selected group of lipids separated the two groups of interest: responders who had a CGI change score of 1-2 and non-responders who had a score of 3-6. FIG. 3 shows the first two principal components plotted to demonstrate the separation of patients who were early responders from the subjects who were not.

Example 4

Antipsychotic Effects

Study II

To confirm the results obtained in Study I, a second study was conducted, Study II. Metabolic changes were to a large extent similar to what was noted with Study I (FIG. 4); however, Study II had a smaller number of patients in the risperidone- and olanzapine-treated groups and hence a lower statistical power and significance. The average number of days of treatment was similar for all antipsychotics in this replication study to partially control for possible differences due to shorter treatment length with aripiprazole in Study I. Treatment with risperidone resulted in significantly increased TG and DG concentrations (FIG. 4) with specific fatty acid changes within each lipid class. The concentrations of PC and PE also increased, but only reached a significance of 0.14 and 0.16. As with Study I, PC18:3n6, PC20:2n6 and PC20:3n6 concentrations in Study II increased (p=0.029, 0.098, 0.090, respectively) while the concentration of PC20:4n6 (arachidonic acid) did not change (FIG. 4).

Olanzapine-treated subjects had increased concentrations of PC, PE, CE, FC, and TG (FIG. 4), however, the small sample size and shorter drug treatment time may have prevented many of the lipid changes from reaching significance. As was seen in Study I, free fatty acids decreased significantly with olanzapine treatment (p=0.02). In addition there were increases in many of the fatty acid metabolites of PE and PC, but no change in the concentration of PC20:4n6 or PE20:4n6 (arachidonic acid) as noted in Study I (FIG. 4). The ratio 20:4n6/20:3n6 also decreased in CE, PE and PC, as was noted in Study I, but did not reach significance. Even with the larger sample set, minimal lipid changes were seen with aripiprazole (TG) in the replication set consistent with Study I findings (FIG. 4). PE concentration increased, but this change did not reach statistical significance. No significant changes were found with the other lipid classes and very little change was seen in the fatty acid concentrations.

Example 5

Pathway Analysis for Drug Effects

To characterize fatty acid elongation and desaturation processes that might be modified in schizophrenia, various ratios of products to substrates in different fatty acid pathways were determined and are summarized in Table VIII. Following treatment with risperidone or olanzapine, the alterations of fatty acid ratios in patients with schizophrenia were essentially reversed toward normal ranges by these atypical antipsychotic drugs. In brief, the ratios of 18:0/16:0, 18:3(n-6)/18:2(n-6), 20:4(n-3)/18:4(n-3), and 22:4(n-6)/20:4(n-6) were all significantly higher, whereas the ratios of 18:1(n-9)/18:0(n-9), 20:4(n-6)/20:3(n-6), 20:5(n-3)/20:4(n-3), 22:5(n-3)/20:5(n-3), 22:6(n-3)/22:5(n-3), and 24:0/22:0 were significantly lower in patients post-treatment than in patients pre-treatment with antipsychotic drugs.

In the present studies, risperidone and olanzapine treatment elevated levels of PE and PC, While there were increases in the n3 and n6 fatty acids in general, levels of arachidonic and docosahexaenoic acids (20:4n6 and 22:6n3) remained essentially the same after treatment (FIG. 1 and FIG. 4) indicating metabolic blocks highlighted in FIGS. 5A and 5B. Both olanzapine and risperidone decreased the apparent delta 5 desaturase activity shown in FIGS. 5A and 5B. This is due to an increase in the concentration of PC20:3n6 with no change in the concentration of PC20:4n6. Both drugs appeared to have profound effects on the concentrations of polyunsaturated fatty acids within the phospholipids.

Arachidonic acid [20:4(n-6)] is mainly synthesized from linoleic acid [18:2(n-6)] by desaturation and elongation (FIGS. 5A and 5B). Linoleic acid, a so-called essential fatty acid, cannot be synthesized by mammals and must be obtained from dietary plant sources. A deficiency of linoleic acid usually leads to a higher content of n-9 trienoic acids, which can be synthesized endogenously (Holman (1973) Essential fatty acid deficiency in humans. In Dietary Lipids and Postnatal Development. Raven Press, New York). An increased level of plasma 20:3(n-9) was not demonstrated in the present studies. Thus, a dietary deficiency of linoleic acid can be reasonably excluded.

The major n-6 pathway consists of a series of desaturation (Δ6 and Δ5 reactions) and elongations (FIGS. 5A and 5B). In normal plasma, the levels of 18:3(n-6) and 22:5(n-6) are very small, with 20:4(n-6) as the major metabolic product of 18:2 (n-6). The decreased level of 20:3(n-6) may lead to an increased ratio of 20:4(n-6)/20:3(n-6) with a normal or possibly increased Δ5 desaturase.

Following treatment with olanzapine or risperidone treatment, Table 5 highlights regulation of pathways for biosynthesis of phosphatidylcholine n-6 fatty acids in schizophrenic patients. Plasma fatty acid compositions were affected minimally in patients after treatment with aripiprazole.

The decreased ratio of 18:0/16:0, but not 24:0/22:0, indicates chain elongation (i.e., 18:0), and was significantly less in patients with schizophrenia than in the normal control subjects. Such a reduction in 18:0 in patients with schizophrenia was essentially reversed after treatment with risperidone or olanzapine (FIG. 1).

Example 6

Events of Relevance to Metabolic Side Effects

The results presented herein showed a marked decrease in free fatty acids accompanied by an increase in TG, indicative of possible effects on lipases (LPL, HSL) involved in storage and release of TG and free fatty acids from adipose tissue. The decrease in free fatty acids may be an effect of the drug reducing lipase activity and fatty acid mobilization. Decreased fatty acid release from adipose tissue together with increased hepatic lipid synthesis could be responsible for the hyperlipidemia and lead to weight gain over time. Following olanzapine or risperidone treatment, the increased triacylglycerol and phospholipid content of the plasma indicates increased presence of very low density lipoproteins.

In addition, the increased cholesterol with olanzapine treatment indicates a potential increase in low density lipoprotein content. For olanzapine, the increased concentrations of 16:1n7, 18:1n7 and 18:1n9 indicates an increase in fatty acid synthesis. An increase in fatty acid synthesis in the risperidone-treated subjects was less evident. Increase in fatty acid biosynthesis upon treatment with several antipsychotic and antidepressant drugs has been noted in cell culture assay systems, implicating a transcription factor in the mechanism of action of these drugs (Ferno, et al. (2005) *Pharmacogenomics J.* 5:298-304; Raeder, et al. (2006) *Neurosci. Lett.* 395; 185-190).

The foregoing is illustrative of the present invention, and is not to be construed as limiting thereof. The invention is defined by the following claims, with equivalents of the claims to be included therein.

That which is claimed is:

1. A method of predicting whether a treatment regimen is effective for treating a central nervous system (CNS) disorder in a mammalian subject, wherein the CNS disorder is schizophrenia, schizophreniform disorder or schizoaffective disorder, and wherein the treatment regimen comprises administration of a typical and/or atypical antipsychotic agent, the method comprising:

(a) detecting a lipid profile of a sample obtained from the subject prior to commencing the treatment regimen, wherein the lipid profile in the sample prior to commencing the treatment regimen correlates with effectiveness of said treatment regimen for the CNS disorder; and (b) predicting whether the treatment regimen is effective for the subject based on the lipid profile in the sample before commencing the treatment regimen.

2. The method of claim 1, wherein the lipid profile evaluates 10 or more lipid metabolites within one or more lipid classes.

3. The method of claim 1, wherein the method comprises detecting a phospholipid metabolite in the sample, wherein a change in the level of the phospholipid metabolite indicates whether the treatment regimen is effective for treating the CNS disorder.

4. The method of claim 3, wherein an increase in the phospholipid metabolite indicates that the treatment regimen is effective for treating the CNS disorder.

5. The method of claim 1, wherein the method comprises detecting the level of a phosphatidylethanolamine metabolite and/or a phosphatidylcholine metabolite, wherein a change in the level of the phosphatidylethanolamine metabolite and/or the phosphatidylcholine metabolite indicates whether the treatment regimen is effective for treating the CNS disorder.

6. The method of claim 1, wherein the method comprises detecting a phospholipid metabolite comprising a polyunsaturated fatty acid moiety, wherein a change in the level of the phospholipid metabolite comprising the polyunsaturated fatty acid moiety indicates whether the treatment regimen is effective for treating the CNS disorder.

7. The method of claim 1, wherein the method comprises detecting a phospholipid metabolite comprising a long chain polyunsaturated fatty acid moiety, wherein a change in the level of the phospholipid metabolite comprising the long chain polyunsaturated fatty acid moiety indicates whether the treatment regimen is effective for treating the CNS disorder.

8. The method of claim 1, wherein the treatment regimen comprises administration of a typical antipsychotic agent.

9. The method of claim 1, wherein the treatment regimen comprises administration of an atypical antipsychotic agent.

10. The method of claim 9, wherein the treatment regimen comprises administration of risperidone, olanzapine and/or aripipirazole.

11. A method of predicting a positive or negative response to a treatment regimen and/or a side effect to a treatment regimen by a mammalian subject with a central nervous system (CNS) disorder, wherein the CNS disorder is schizophrenia, schizophreniform disorder or schizoaffective disorder, and wherein the treatment regimen comprises administration of a typical and/or atypical antipsychotic agent, the method comprising:

(a) detecting a lipid profile of a sample obtained from the subject following commencement of the treatment regimen and before the positive or negative response and/or the side effect can be detected, wherein the lipid profile after commencing the treatment regimen is correlated with a positive or negative response to the treatment regimen and/or to a side effect from the treatment regimen; and (b) predicting whether the subject is responding positively or negatively to the treatment regimen and/or is developing a side effect from the treatment regimen based on the lipid profile in the sample.

12. The method of claim 11, wherein the lipid profile is obtained within 1 week of commencing the treatment regimen.

13. The method of claim 11, wherein the lipid profile evaluates 10 or more lipid metabolites within one or more lipid classes.

14. The method of claim 11, wherein the method further comprises detecting the lipid profile of a sample from the subject prior to commencing the treatment regimen and comparing with a lipid profile after commencement of the treatment regimen.

15. The method of claim 11, wherein the method comprises detecting a phospholipid metabolite in the sample, wherein a change in the level of the phospholipid metabolite indicates whether the subject is responding positively or negatively to the treatment regimen.

16. The method of claim 11, wherein the method comprises detecting the level of a phosphatidylethanolamine metabolite and/or a phosphatidylcholine metabolite, wherein a change in the level of the phosphatidylethanolamine metabolite and/or the phosphatidylcholine metabolite indicates whether the subject is responding positively or negatively to the treatment regimen.

17. The method of claim 11, wherein the method comprises detecting a phospholipid metabolite comprising a polyunsaturated fatty acid moiety, wherein a change in the level of the phospholipid metabolite comprising the polyunsaturated fatty acid moiety indicates whether the subject is responding positively or negatively to the treatment regimen.

18. The method of claim 11, wherein the method comprises detecting a phospholipid metabolite comprising a long chain polyunsaturated fatty acid moiety, wherein a change in the level of the phospholipid metabolite comprising the long chain polyunsaturated fatty acid moiety indicates whether the subject is responding positively or negatively to the treatment regimen.

19. The method of claim 11, wherein an increase in the phospholipid metabolite after commencement of the treatment regimen indicates that the subject is responding positively to the treatment regimen.

20. The method of claim 11, wherein the treatment regimen comprises administration of a typical antipsychotic drug.

21. The method of claim 11, wherein the treatment regimen comprises administration of an atypical antipsychotic drug.

22. The method of claim 21, wherein the treatment regimen comprises administration of risperidone.

23. The method of claim 22, wherein the method comprises detecting the level of a phospholipid metabolite in Table III, wherein a change in the level of the phospholipid metabolite as shown in Table III indicates that the subject is responding positively to the treatment regimen.

24. The method of claim 22, wherein the method comprises detecting the level of a free fatty acid metabolite and/or a triacylglycerol metabolite in Table III, wherein a change in the level of the free fatty acid metabolite and/or triacylglycerol metabolite as shown in Table III indicates that the subject is responding positively to the treatment regimen.

25. The method of claim 22, wherein the method comprises detecting a level of a lipid metabolite in Table III, wherein a change in the level of the lipid metabolite as shown in Table III indicates that the subject is responding positively to the treatment regimen and/or is developing a side effect to the treatment regimen.

26. The method of claim 21, wherein the treatment regimen comprises administration of olanzapine.

27. The method of claim 26, wherein the method comprises detecting a level of a lipid metabolite in Table IV, wherein a change in the level of the lipid metabolite as shown in Table IV indicates that the subject is responding positively to the treatment regimen and/or is developing a side effect to the treatment regimen.

28. The method of claim 26, wherein the method comprises detecting the level of a phospholipid metabolite in Table IV, wherein a change in the level of the phospholipid metabolite as shown in Table IV indicates that the subject is responding positively to the treatment regimen.

29. The method of claim 26, wherein the method comprises detecting the level of a free fatty acid metabolite and/or a triacylglycerol metabolite in Table IV, wherein a change in the level of the free fatty acid metabolite and/or triacylglycerol metabolite as shown in Table IV indicates that the subject is responding positively to the treatment regimen.

30. The method of claim 21, wherein the treatment regimen comprises administration of aripiprazole.

31. The method of claim 30, wherein the method comprises detecting a level of a lipid metabolite in Table V, wherein a change in the level of the lipid metabolite as shown in Table V indicates that the subject is responding positively to the treatment regimen and/or is developing a side effect to the treatment regimen.

32. The method of claim 30, wherein the method comprises detecting the level of a phospholipid metabolite in Table V, wherein a change in the level of the phospholipid metabolite as shown in Table V indicates that the subject is responding positively to the treatment regimen.

33. The method of claim 30, wherein the method comprises detecting the level of a free fatty acid metabolite and/or a triacylglycerol metabolite in Table V, wherein a change in the level of the free fatty acid metabolite and/or triacylglycerol metabolite as shown in Table V indicates that the subject is responding positively to the treatment regimen.

34. The method of claim 11, wherein the method comprises detecting an amount of a lipid metabolite in Table I, wherein a reversal of the change in the amount of the lipid metabolite as shown in Table I after commencement of the treatment regimen indicates that the subject is responding positively to the treatment regimen.

35. The method of claim 11, wherein the method comprises detecting a mole % within class of a lipid metabolite in Table II, wherein a reversal of the change in the mole % within class of the lipid metabolite as shown in Table II after commencement of the treatment regimen indicates that the subject is responding positively to the treatment regimen.

36. The method of claim 11, wherein the method comprises detecting a phospholipid metabolite comprising an n3, n6 and/or n9 fatty acid moiety, wherein an increase in the phospholipid metabolite comprising an n3, n6 and/or n9 fatty acid moiety after commencement of the treatment regimen indicates that the subject is responding positively to the treatment regimen.

37. The method of claim 11, wherein the method comprises detecting a phosphatidylethanolamine metabolite comprising a 16:0, 18:0 and/or 18:1 fatty aldehyde moiety, wherein an increase in the phosphatidylethanolamine metabolite comprising a 16:0, 18:0 and/or 18:1 fatty aldehyde moiety after commencement of the treatment regimen indicates that the subject is responding positively to the treatment regimen.

38. The method of claim 11, wherein the side effect comprises weight gain, hyperlipidemia, hyperglycemia, risk of developing metabolic syndrome, risk of developing diabetes mellitus, risk of developing cardiovascular complications, or any combination thereof.

39. The method of claim 11, wherein if the subject is predicted to be responding negatively to the treatment regimen and/or to be developing a side effect to the treatment regimen, the treatment regiment is discontinued, a different treatment regimen is implemented and/or a supplemental therapy is administered.

40. A method of determining a positive or negative response to a treatment regimen and/or a side effect to a treatment regimen by a mammalian subject with a central nervous system (CNS) disorder, wherein the CNS disorder is schizophrenia, schizophreniform disorder or schizoaffective disorder, and wherein the treatment regimen comprises administration of a typical and/or atypical antipsychotic agent, the method comprising:
(a) detecting a lipid profile of a sample obtained from the subject following commencement of the treatment regimen, wherein the lipid profile is obtained within 2 weeks of commencing the treatment regimen, wherein the lipid profile after commencing the treatment regimen is correlated with a positive or negative response to the treatment regimen and/or to a side effect from the treatment regimen; and
(b) determining whether the subject is responding positively or negatively to the treatment regimen and/or is developing a side effect from the treatment regimen based on the lipid profile in the sample before the positive or negative response and/or the side effect can be detected.

* * * * *

UNITED STATES PATENT AND TRADEMARK OFFICE
CERTIFICATE OF CORRECTION

PATENT NO. : 8,637,321 B2
APPLICATION NO. : 12/091213
DATED : January 28, 2014
INVENTOR(S) : Kaddurah-Daouk et al.

It is certified that error appears in the above-identified patent and that said Letters Patent is hereby corrected as shown below:

In the Specification:

Column 3, Line 58: Please correct "(2002) δ:" to read -- (2002) 8: --

Column 25, Line 56: Please correct "resperidone," to read -- risperidone, --

Column 27, Line 3: Please correct "resperidone," to read -- risperidone, --
         Line 7: Please correct "resperidone," to read -- risperidone, --

Column 30, Line 50: Please correct "resperidone," to read -- risperidone, --
         Line 64: Please correct "resperidone" to read -- risperidone --

Column 31, Line 3: Please correct "resperidone" to read -- risperidone --

Column 40, Line 20, after "Z-values" on Line 20, please insert the following:

--  were used to evaluate if there was a treatment effect. For the smallest p value that could be obtained by chance, there were at least five smaller p-values in the olanzapine group and 22 smaller p-values in the risperidone group. The distribution of p-values in the aripiprazole group was similar to the control subjects.
   Heat maps were used to visualize differences between schizophrenic patients and healthy controls as well as the differences in the treatment effects in schizophrenic patients. Heat maps were created by testing the significance of each treatment on the metabolite concentration using a paired Student's t-test (for the baseline study that compares controls and patients, unpaired Student's t-test was used). If the treatment effect was significant at alpha of 0.05, a mean percentage difference in the concentration of the metabolite induced by treatment was calculated. The heatmap can be read as follows: the column headers display the fatty acid and the row headers the family of fatty acids present in each lipid class. Each cell in the heatmap represents a standardized observation for a particular metabolite. Metabolites significantly increased by treatment were displayed in red, Signed and Sealed this
Twenty-first Day of October, 2014

Michelle K. Lee
*Deputy Director of the United States Patent and Trademark Office* while metabolites significantly decreased by treatment were displayed in green. The brightness of each color corresponded to the magnitude of the difference in quartiles. The brighter the square is the larger the difference.

Logistic regression was used to identify a set of pretreatment lipid metabolites that were related to drug response. Principal component analysis (PCA) was then used to examine how well a selected group of lipids separates two groups of interest: responders who had a CGI change score of 1-2 and non-responders who had a score of 3-6. Principle component analysis (PCA) is a way to explain the variance-covariance structure of a set of variables through a few linear combinations of those variables. Its general objectives are data reduction, interpretation, and dealing with highly correlated variables. PCA can reveal relationships that were not previously suspected, and allow a novel interpretation of the data.

Example 2

Baseline Analyses

At baseline, and prior to administration of antipsychotic medications, the level of eight lipid classes between 27 schizophrenic patients (Study 1) and 16 healthy controls were compared. These lipid classes were CE, FC, TG, DG, FA, LY, PC, PE. The heatmap (FIG. 1A) shows fatty acids within the eight lipid classes that are significantly different between patients with schizophrenia and controls (see statistics in Example 1). The column headers display the fatty acid and the row headers the family of fatty acids present in each lipid class. Metabolites significantly higher in --

Column 41, Lines 4-55, after "(p=0.01,0.009)," on Line 4, Please delete the following:

"were used to evaluate if there was a treatment effect. For the smallest p value that could be obtained by chance, there were at least five smaller p-values in the olanzapine group and 22 smaller p-values in the risperidone group. The distribution of p-values in the aripiprazole group was similar to the control subjects.

Heat maps were used to visualize differences between schizophrenic patients and healthy controls as well as the differences in the treatment effects in schizophrenic patients. Heat maps were created by testing the significance of each treatment on the metabolite concentration using a paired Student's t-test (for the baseline study that compares controls and patients, unpaired Student's t-test was used). If the treatment effect was significant at alpha of 0.05, a mean percentage difference in the concentration of the metabolite induced by treatment was calculated. The heatmap can be read as follows: the column headers display the fatty acid and the row headers the family of fatty acids present in each lipid class. Each cell in the heatmap represents a standardized observation for a particular metabolite. Metabolites significantly increased by treatment were displayed in red, while metabolites significantly decreased by treatment were displayed in green. The brightness of each color corresponded to the magnitude of the difference in quartiles. The brighter the square is the larger the difference.

Logistic regression was used to identify a set of pretreatment lipid metabolites that were related to drug response. Principal component analysis (PCA) was then used to examine how well a selected group of lipids separates two groups of interest: responders who had a CGI change score of 1-2 and non-responders who had a score of 3-6. Principle component analysis (PCA) is a way to explain the variance-covariance structure of a set of variables through a few linear combinations of those variables. Its general objectives are data reduction, interpretation, and dealing with highly correlated variables. PCA can reveal relationships that were not previously suspected, and allow a novel interpretation of the data.

Example 2

Baseline Analyses

At baseline, and prior to administration of antipsychotic medications, the level of eight lipid classes between 27 schizophrenic patients (Study 1) and 16 healthy controls were compared. These lipid classes were CE, FC, TG, DG, FA, LY, PC, PE. The heatmap (FIG. 1A) shows fatty acids within the eight lipid classes that are significantly different between patients with schizophrenia and controls (see statistics in Example 1). The column headers display the fatty acid and the row headers the family of fatty acids present in each lipid class. Metabolites significantly higher in"